(12) United States Patent
Yencho et al.

(10) Patent No.: US 7,004,949 B2
(45) Date of Patent: Feb. 28, 2006

(54) METHOD AND SYSTEM FOR ATTACHING A GRAFT TO A BLOOD VESSEL

(75) Inventors: Stephen A. Yencho, Menlo Park, CA (US); Bernard A. Hausen, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 428 days.

(21) Appl. No.: 09/886,074

(22) Filed: Jun. 18, 2001

(65) Prior Publication Data

US 2001/0037139 A1 Nov. 1, 2001

Related U.S. Application Data

(63) Continuation of application No. 09/132,711, filed on Aug. 12, 1998, now Pat. No. 6,461,320.

(51) Int. Cl.
*A61B 17/08* (2006.01)

(52) U.S. Cl. .................. 606/142; 606/153; 606/155

(58) Field of Classification Search .............. 606/151, 606/153, 154, 155, 156, 108, 213, 157, 158, 606/167, 179, 184, 185, 139, 142, 143
See application file for complete search history.

(56) References Cited

U.S. PATENT DOCUMENTS

| | | | |
|---|---|---|---|
| 3,254,650 A | 6/1966 | Collito | |
| 3,254,651 A | 6/1966 | Collito | |
| 3,519,187 A | 7/1970 | Kapitanov et al. | |
| 3,774,615 A | 11/1973 | Lim et al. | |
| 4,118,806 A | 10/1978 | Porier et al. | |
| 4,214,587 A | 7/1980 | Sakura, Jr. | |
| 4,217,664 A | 8/1980 | Faso | |
| 4,337,420 A | 6/1982 | Kalmanash | |
| 4,350,160 A | 9/1982 | Kolesov et al. | |
| 4,352,358 A | 10/1982 | Angelchik | |
| 4,366,819 A | 1/1983 | Kaster | |
| 4,368,736 A | 1/1983 | Kaster | |
| 4,503,568 A | 3/1985 | Madras | |
| 4,523,592 A | 6/1985 | Daniel | |
| 4,534,761 A | 8/1985 | Raible | |
| 4,553,542 A | 11/1985 | Schenck et al. | |
| 4,577,631 A | 3/1986 | Kreamer | |
| 4,589,416 A | 5/1986 | Green | |

(Continued)

FOREIGN PATENT DOCUMENTS

DE 29713335 11/1997

(Continued)

OTHER PUBLICATIONS

"Cardica PAS-Port Proximal Anastomosis System 510(k)", Section VI.C., "Substantial Equvalence", and Attachment 7, (unpublished).

(Continued)

*Primary Examiner*—Anhtuan T. Nguyen
*Assistant Examiner*—Jessica R Baxter
(74) *Attorney, Agent, or Firm*—Brian A. Schar; Cindy A. Lynch

(57) ABSTRACT

Anastomotic stents for connecting a graft vessel to a target vessel, and methods of use thereof. The anastomotic stents of the invention are suitable for use in a variety of anastomosis procedures, including coronary artery bypass grafting. One embodiment of the invention comprises a large vessel anastomotic stent for use with large diameter target vessels such as the aorta or its major side branches. Another embodiment of the invention comprises a small vessel anastomotic stent for use on a target vessel which has a small diameter such as a coronary artery. Another aspect of the invention involves applicators for use with the stents of the invention.

16 Claims, 20 Drawing Sheets

U.S. PATENT DOCUMENTS

| | | |
|---|---|---|
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,861,330 A | 8/1989 | Voss |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,193,731 A | 3/1993 | Aranyi |
| 5,205,459 A | 4/1993 | Brinkerhoff et al. |
| 5,211,683 A | 5/1993 | Maginot |
| 5,217,474 A | 6/1993 | Zacca et al. |
| 5,221,281 A | 6/1993 | Klicek |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,478,354 A | 12/1995 | Tovey et al. |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,643,340 A | 7/1997 | Nunokawa |
| 5,645,520 A | 7/1997 | Nakamura et al. |
| 5,657,429 A | 8/1997 | Wang et al. |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,762,458 A | 6/1998 | Wang et al. |
| 5,779,718 A | 7/1998 | Green et al. |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |
| 5,841,950 A | 11/1998 | Wang et al. |
| 5,855,583 A | 1/1999 | Wang et al. |
| 5,868,763 A | 2/1999 | Spence et al. |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | Lemole |
| 5,904,697 A | 5/1999 | Gifford, III et al. |
| 5,907,664 A | 5/1999 | Wang et al. |
| 5,911,036 A | 6/1999 | Wright et al. |
| 5,915,616 A | 6/1999 | Viola et al. |
| 5,921,995 A | 7/1999 | Kleshinski |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,976,159 A | 11/1999 | Bolduc et al. |
| 5,976,178 A * | 11/1999 | Goldsteen et al. .......... 606/151 |
| 6,001,124 A | 12/1999 | Bachinski |
| 6,007,544 A | 12/1999 | Kim |
| 6,007,576 A * | 12/1999 | McClellan ............... 623/23.64 |
| 6,013,190 A | 1/2000 | Berg et al. |
| 6,015,416 A | 1/2000 | Stefanchik et al. |
| 6,022,367 A | 2/2000 | Sherts |
| 6,024,748 A | 2/2000 | Manzo et al. |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinkski et al. |
| 6,036,703 A | 3/2000 | Evans et al. |
| 6,036,704 A | 3/2000 | Yoon |
| 6,036,705 A | 3/2000 | Nash et al. |
| 6,050,472 A | 4/2000 | Shibata |
| 6,053,390 A | 4/2000 | Green et al. |
| 6,056,762 A | 5/2000 | Nash et al. |
| 6,066,144 A | 5/2000 | Wolf et al. |
| 6,066,148 A | 5/2000 | Rygaard |

| | | | |
|---|---|---|---|
| 6,068,637 A | 5/2000 | Popov et al. | |
| 6,074,416 A | 6/2000 | Berg et al. | |
| 6,080,167 A | 6/2000 | Lyell | |
| 6,080,173 A | 6/2000 | Williamson, IV et al. | |
| 6,083,234 A | 7/2000 | Nicholas et al. | |
| 6,110,188 A | 8/2000 | Narciso, Jr. | |
| 6,113,612 A | 9/2000 | Swanson et al. | |
| 6,117,148 A | 9/2000 | Ravo et al. | |
| 6,120,432 A | 9/2000 | Sullivan et al. | |
| 6,146,393 A | 11/2000 | Wakabayashi | |
| 6,149,681 A | 11/2000 | Houser et al. | |
| 6,152,937 A | 11/2000 | Peterson et al. | |
| 6,152,945 A | 11/2000 | Bachinski et al. | |
| 6,165,185 A | 12/2000 | Shennib et al. | |
| 6,167,889 B1 | 1/2001 | Benetti | |
| 6,171,319 B1 | 1/2001 | Nobles et al. | |
| 6,171,321 B1 | 1/2001 | Gifford, III et al. | |
| 6,176,413 B1 | 1/2001 | Heck et al. | |
| 6,176,864 B1 | 1/2001 | Chapman | |
| 6,186,942 B1 | 2/2001 | Sullivan et al. | |
| 6,187,019 B1 | 2/2001 | Stefanchik et al. | |
| 6,187,020 B1 | 2/2001 | Zegdi et al. | |
| 6,190,396 B1 | 2/2001 | Whitin et al. | |
| 6,190,397 B1 | 2/2001 | Spence et al. | |
| 6,190,590 B1 | 2/2001 | Randall et al. | |
| 6,193,129 B1 | 2/2001 | Bittner et al. | |
| 6,193,734 B1 | 2/2001 | Bolduc et al. | |
| 6,206,912 B1 | 3/2001 | Goldsteen et al. | |
| 6,206,913 B1 | 3/2001 | Yencho et al. | |
| 6,235,054 B1 | 5/2001 | Berg et al. | |
| 6,241,743 B1 * | 6/2001 | Levin et al. | 606/153 |
| 6,251,116 B1 | 6/2001 | Shennib et al. | |
| 6,293,955 B1 * | 9/2001 | Houser et al. | 606/153 |
| 6,371,964 B1 * | 4/2002 | Vargas et al. | 606/153 |
| 6,428,550 B1 * | 8/2002 | Vargas et al. | 606/153 |
| 6,458,140 B1 | 10/2002 | Akin et al. | |
| 6,464,709 B1 | 10/2002 | Shennib et al. | |
| 6,485,496 B1 | 11/2002 | Suyker et al. | |

FOREIGN PATENT DOCUMENTS

| | | |
|---|---|---|
| DE | 19732234 | 1/1999 |
| EP | 0 701 800 | 3/1996 |
| EP | 0 517 252 | 12/1996 |
| EP | 0 885 595 | 12/1998 |
| EP | 0 820 724 | 1/2000 |
| EP | 0 820 725 | 1/2000 |
| EP | 0 913 125 | 7/2000 |
| EP | 0 938 870 | 9/2000 |
| EP | 0 990 420 | 12/2000 |
| FR | 2316910 | 2/1977 |
| WO | 92/08513 | 5/1992 |
| WO | 96/25886 | 8/1996 |
| WO | 97/25002 | 7/1997 |
| WO | 97/27898 | 8/1997 |
| WO | 97/31575 | 9/1997 |
| WO | 97/47261 | 12/1997 |
| WO | 98/07399 | 2/1998 |
| WO | 98/19608 | 5/1998 |
| WO | 98/19618 | 5/1998 |
| WO | 98/19625 | 5/1998 |
| WO | 98/19629 | 5/1998 |
| WO | 98/19630 | 5/1998 |
| WO | 98/19631 | 5/1998 |
| WO | 98/19632 | 5/1998 |
| WO | 98/19634 | 5/1998 |
| WO | 98/19636 | 5/1998 |
| WO | 98/30153 | 7/1998 |
| WO | 98/3/7814 | 9/1998 |
| WO | 98/40036 | 9/1998 |
| WO | 98/42262 | 10/1998 |
| WO | 98/47430 | 10/1998 |
| WO | 98/55027 | 12/1998 |
| WO | 99/08603 | 2/1999 |
| WO | 99/11178 | 3/1999 |
| WO | 99/17665 | 4/1999 |
| WO | 99/18887 | 4/1999 |
| WO | 99/21491 | 5/1999 |
| WO | 99/37218 | 7/1999 |
| WO | 99/38441 | 8/1999 |
| WO | 99/38454 | 8/1999 |
| WO | 99/40851 | 8/1999 |
| WO | 99/40868 | 8/1999 |
| WO | 99/45848 | 9/1999 |
| WO | 99/52481 | 10/1999 |
| WO | 99/62406 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/09040 | 2/2000 |
| WO | 00/10486 | 3/2000 |
| WO | 00/12013 | 3/2000 |
| WO | 00/15144 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/27310 | 5/2000 |
| WO | 00/27311 | 5/2000 |
| WO | 00/27312 | 5/2000 |
| WO | 00/27313 | 5/2000 |
| WO | 00/33745 | 6/2000 |
| WO | 00/41633 | 7/2000 |
| WO | 00/53104 | 9/2000 |
| WO | 00/56223 | 9/2000 |
| WO | 00/56226 | 9/2000 |
| WO | 00/56227 | 9/2000 |
| WO | 00/56228 | 9/2000 |
| WO | 00/59380 | 10/2000 |
| WO | 00/66007 | 11/2000 |
| WO | 00/66009 | 11/2000 |
| WO | 00/69343 | 11/2000 |
| WO | 00/69346 | 11/2000 |
| WO | 00/69349 | 11/2000 |
| WO | 00/69364 | 11/2000 |
| WO | 00/72764 | 12/2000 |
| WO | 00/74579 | 12/2000 |
| WO | 00/76405 | 12/2000 |
| WO | 01/08601 | 2/2001 |
| WO | 01/12074 | 2/2001 |
| WO | 01/15607 | 3/2001 |
| WO | 01/17440 | 3/2001 |
| WO | 01/19257 | 3/2001 |
| WO | 01/19259 | 3/2001 |
| WO | 01/19284 | 3/2001 |
| WO | 01/34037 | 5/2001 |
| WO | WO 200230172 A2 * | 4/2002 |

OTHER PUBLICATIONS

Sales training brochure entitled "Cor-Link Automated Anastomosis Device" (2002).

* cited by examiner

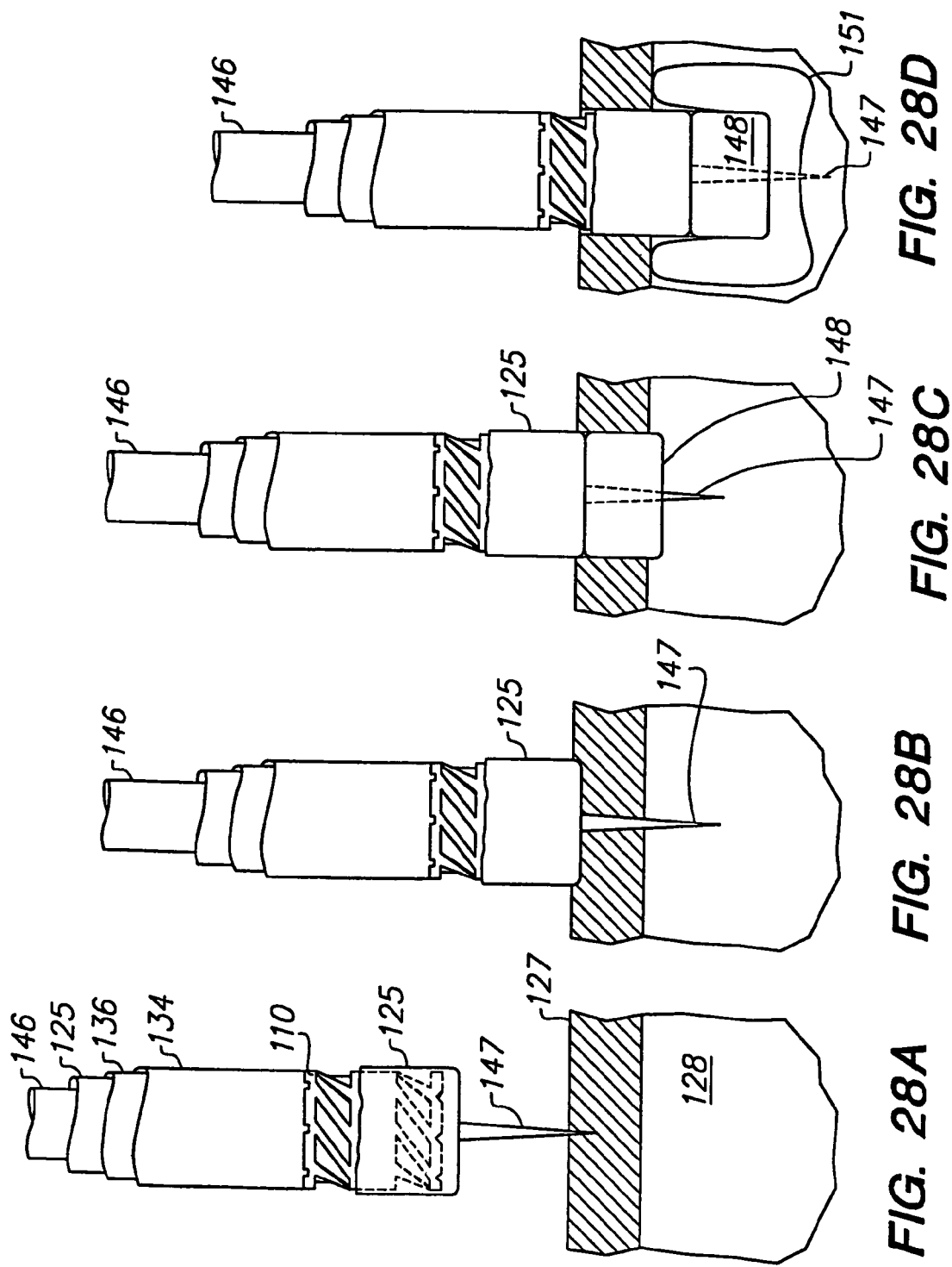

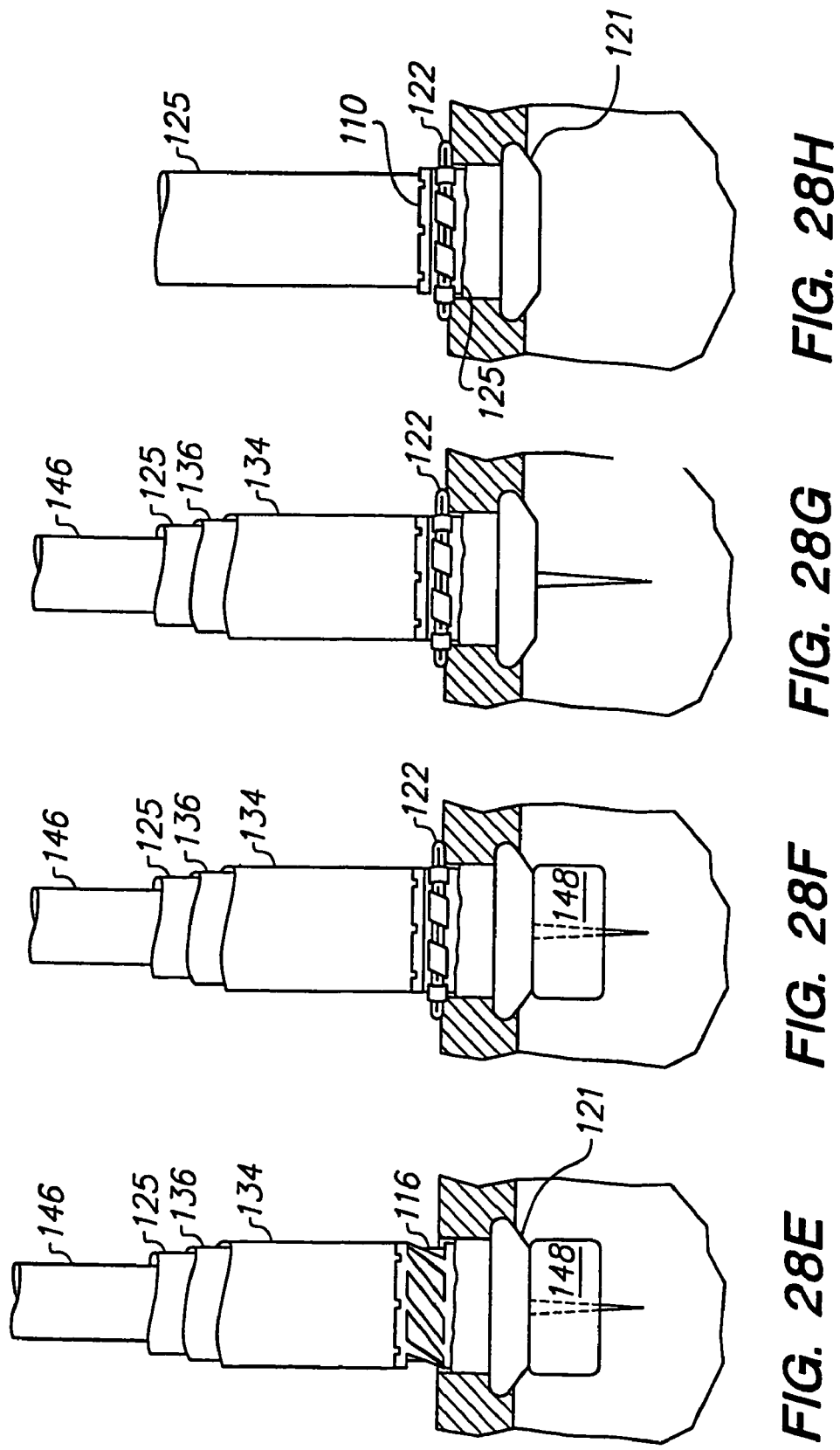

METHOD AND SYSTEM FOR ATTACHING A GRAFT TO A BLOOD VESSEL

This application is a continuation of application Ser. No. 09/132,711, filed on Aug. 12, 1998, now U.S. Pat. No. 6,461,320.

BACKGROUND OF THE INVENTION

This invention generally relates to devices and methods for performing a vascular anastomosis, and more particularly to stents for securing a graft vessel to a target vessel.

Vascular anastomoses, in which two vessels within a patient are surgically joined together to form a continuous channel, are required for a variety of conditions including coronary artery disease, diseases of the great and peripheral vessels, organ transplantation, and trauma. For example, in coronary artery disease (CAD), an occlusion or stenosis in a coronary artery interferes with blood flow to the heart muscle. In order to restore adequate blood flow to the heart, a graft vessel in the form of a prosthesis or harvested artery or vein is used to reroute blood flow around the occlusion. The treatment, known as coronary artery bypass grafting (CABG), can be highly traumatic to the patient's system.

In conventional CABG a large incision is made in the chest and the sternum is sawed in half to allow access to the heart. In addition, cardiopulmonary bypass, in which the patient's blood is circulated outside of the body through a heart-lung machine, is used so that the heart can be stopped and the anastomosis performed. In order to minimize the trauma to the patient's system induced by conventional CABG, less invasive techniques have been developed in which the surgery is performed through small incisions in the patient's chest with the aid of visualizing scopes. Less invasive CABG can be performed on a beating or a non-beating heart and thus may avoid the need for cardiopulmonary bypass.

In both conventional and less invasive CABG, the surgeon has to suture the graft vessel in place between the coronary artery and a blood supplying vein or artery. The suturing procedure is a time consuming, difficult process requiring a high level of surgical skill. In order to perform the suturing procedure, the surgeon must have relatively unobstructed access to the anastomotic site within the patient. As a result, in less invasive approaches which provide only limited access to the patient's vessels, some of the major coronary vessels cannot be reached adequately, which can result in incomplete revascularization and a resulting negative effect on patient survival. Moreover, certain target vessels, such as heavily calcified coronary vessels, vessels having a very small diameter of less than about 1 mm, and previously bypassed vessels, may make the suturing process difficult or impossible, so that a sutured anastomosis is not possible.

Additionally, a common problem with CABG has been the formation of thrombi and atherosclerotic lesions at and around the grafted artery, which can result in the reoccurrence of ischemia. Moreover, second operations necessitated by the reoccurrence of arterial occlusions are technically more difficult and risky due to the presence of the initial bypass. For example, surgeons have found it difficult to saw the sternum in half during the next operation without damaging the graft vessels from the first bypass which are positioned behind the sternum.

Therefore, it would be a significant advance to provide a sutureless vascular anastomosis in which the graft vessels can be positioned on a variety of locations on target vessels having a variety of different diameters, which is easily performed, and which minimizes thrombosis associated with the anastomosis. The present invention satisfies these and other needs.

SUMMARY OF THE INVENTION

The invention is directed to anastomotic stents for connecting a graft vessel to a target vessel, and methods of use thereof. The anastomotic stents of the invention are suitable for use in a variety of anastomosis procedures, including coronary artery bypass grafting. The term "target vessel" refers to vessels within the patient which are connected to either or both of the upstream and the downstream end of the graft vessel. One embodiment of the invention comprises a large vessel anastomotic stent for use with large diameter target vessels such as the aorta or its major side branches. Another embodiment of the invention comprises a small vessel anastomotic stent for use on a target vessel which has a small diameter such as a coronary artery. Another aspect of the invention involves applicators for use with the stents of the invention. The terms "distal" and "proximal" as used herein refer to positions on the stents or applicators relative to the physician. Thus, the distal end of the stent is further from the physician than is the stent proximal end. The proximal end of an implanted stent is further from the center of the target vessel lumen than is the stent distal end.

The large vessel anastomotic stents of the invention generally comprise a substantially cylindrical body having a longitudinal axis, an open proximal end, an open distal end, a lumen therein, and at least one deformable section which radially expands to form a flange. The stent, with one end of a graft vessel attached thereto, is inserted into an incision in a wall of the target vessel with the deformable section in a first configuration, and the deformable section is radially expanded to a second configuration to deploy the flange. The flange applies an axial force, substantially aligned with the stent longitudinal axis, against the wall of the target vessel. Additionally, the flange is configured to apply a radial force, substantially transverse to the stent longitudinal axis, against the wall of the target vessel, to secure the stent to the target vessel.

In one embodiment of the large vessel stent, the stent has a single deformable section forming a flange, preferably on a distal section of the stent. However, a plurality of deformable sections may be provided on the stent. For example, in an alternative embodiment, the stent has a second deformable section on a proximal section of the stent. With the proximal and distal end flanges deployed, the stent is prevented from shifting proximally out of the target vessel or distally further into the interior of the target vessel.

The large vessel stents of the invention are configured to connect to target vessels of various sizes having a wall thickness of at least about 0.5 mm, and typically about 0.5 mm to about 5 mm. In one embodiment of the invention, the large vessel anastomotic stent is configured to longitudinally collapse as the deformable section is radially expanded. The surgeon can control the longitudinal collapse to thereby position the distal end flange at a desired location at least partially within the incision in the target vessel wall. Moreover, in the embodiment having a proximal end flange, the surgeon can control the position of the proximal end flange by longitudinally collapsing the stent to a greater or lesser degree, to thereby position the proximal end flange at a desired location in contact with the target vessel. Thus, regardless of the thickness of the target vessel wall, the stent can be longitudinally collapsed to position the flanges against the target vessel wall and effectively connect the stent thereto. This feature is significant because the stent must be connected to target vessels which have a wide range of wall thickness. For example, the aortic wall thickness is typically about 1.4 mm to about 4.0 mm. Therefore, regardless of the thickness of the target vessel wall, the degree of deployment of the proximal end flange, and thus the longitudinal collapse of the stent, can be controlled by the physician to thereby effectively connect the stent to the target vessel. For example, the surgeon may choose between partially deploying the proximal end flange so that it is positioned against an outer surface of the target vessel wall, or fully deploying the flange to position it in contact with the media of the target vessel wall within the incision in the target vessel wall.

In a presently preferred embodiment, the graft vessel is attached to the stent before insertion into the patient by placing the graft vessel within the lumen of the stent, and everting the end of the graft vessel out the stent distal end and about at least the distal deformable section. In a presently preferred embodiment, the graft vessel is everted about at least the section which contacts the media of the target vessel wall proximal to the distal deformable section, to facilitate sealing at the anastomosis site.

In a presently preferred embodiment of the invention, the deformable section on the large vessel stent comprises a plurality of helical members interconnected and disposed circumferentially around the stent. By rotating the distal end and the proximal end of the stent relative to one another, the helical members radially expand and the stent longitudinally collapses to form the flange. In a presently preferred embodiment, the distal flange is configured to deploy before the proximal end flange.

Another aspect of the invention comprises the applicators designed for introducing and securing the large vessel anastomotic stents of the invention to the target vessel. One such applicator is configured to apply torque and axial compressive load to the large vessel stent, to thereby radially expand the deformable section which forms the flange. The applicator of the invention may be provided with a sharp distal end, to form an incision in the target vessel wall through which the stent is inserted or to otherwise facilitate insertion of the stent into the target vessel wall. Another embodiment of the applicator of the invention includes a catheter member having one or more inflatable members designed to expand the incision in the target vessel and introduce the large vessel stent therein.

Another embodiment of the invention comprises small vessel anastomotic stents for use on small target vessels such as coronary arteries. The small vessel stents generally comprise an outer flange configured to be positioned adjacent an outer surface of the target vessel, and an inner flange configured to be positioned against an inner surface of the target vessel and connected to the outer flange. The outer and inner flanges generally comprise a body defining an opening, with one end of the graft vessel secured to the outer flange.

The small vessel anastomotic stents of the invention are used on small target vessels having a wall thickness of less than about 1.0 mm, and typically about 0.1 mm to about 1 mm. For example, small target vessels include coronary arteries. Despite the small size of the target vessels, the small vessel stents of the invention provide sutureless connection without significantly occluding the small inner lumen of the target vessel or impeding the blood flow therethrough.

In a presently preferred embodiment of the invention, the graft vessel is received into the opening in the outer flange and everted around the body of the outer flange to connect to the outer flange. In another embodiment, as for example when the graft vessel is a mammary artery, the graft vessel is connected to the outer flange by connecting members such as sutures, clips, hooks, and the like.

The outer flange, with the graft vessel connected thereto, is loosely connected to the inner flange before insertion into the patient. The space between the loosely connected inner and outer flanges is at least as great as the wall thickness of the target vessel so that the inner flange can be inserted through an incision in the target vessel and into the target vessel lumen, with the outer flange outside the target vessel. With the outer and inner flanges in place on either side of a wall of the target vessel, tightening the flanges together compresses a surface of the graft vessel against the outer surface of the target vessel. This configuration forms a continuous channel between the graft vessel and the target vessel, without the need to suture the graft vessel to the target vessel wall and preferably without the use of hooks or barbs which puncture the target vessel.

In one embodiment of the invention, the inner flange is introduced into the target vessel in a folded configuration and thereafter unfolded into an expanded configuration inside the target vessel. The folded configuration reduces the size of the inner flange so that the size of the incision in the target vessel wall can be minimized. Folding the flange minimizes trauma to the target vessel and restenosis, and facilitates sealing between the graft and target vessel at the anastomotic site.

In a presently preferred embodiment of the invention, the inner and outer flanges are connected together by prongs on one member configured to extend through the body of the other member. However, the inner and outer flanges may be connected together by a variety of different types of connecting members such as sutures, hooks, clips, and the like. In a presently preferred embodiment, the flange members are connected together by prongs on the inner member configured to extend through the incision in the target vessel wall, without puncturing the wall of the target vessel, and through prong receiving openings in the body of the outer flange. The prong receiving openings in the outer flange may be configured to allow for the forward movement of the prong through the opening to bring the inner and outer flanges together, but prevent the backward movement of the prong out of the opening, so that the inner and outer flanges remain substantially compressed together to seal the anastomotic site.

Another aspect of the invention comprises a small vessel stent applicator which facilitates introduction of the inner flange into the target vessel lumen, and connection of the inner flange to the outer flange around the target vessel. In one embodiment of the small vessel stent applicator, the applicator folds the inner flange into the folded configuration for introduction into the lumen of the target vessel.

Anastomotic systems of the invention may comprise combinations of the large and small vessel stents of the invention, for connecting one or both ends of a graft vessel to target vessels. Typically, in a coronary bypass using the anastomotic system of the invention, a large vessel stent connects the proximal end of the graft vessel to the aorta, and a small vessel stent connects the distal end of the graft vessel to an occluded coronary artery. However, it will be apparent to one of ordinary skill in the art that various combinations and uses of the anastomotic stents of the invention may be used. For example, in patients with an extreme arteriosclerotic lesion in the aorta, which may result in serious complications during surgical procedures on the aorta, the anastomotic stents of the invention allow the surgeon to avoid this region and connect the proximal end of the graft vessel to any other adjacent less diseased vessel, such as the arteries leading to the arms or head.

The large and small vessel stents of the invention are provided in a range of sizes for use on various sized graft vessels. Thus, the anastomotic stents of the invention can be used with venous grafts, such as a harvested saphenous vein graft, arterial grafts, such as a dissected mammary artery, or a synthetic prosthesis, as required.

Connection of the large vessel stent does not require the stoppage of blood flow in the target vessel. Moreover, the anastomotic stents of the invention can be connected to the target vessel without the use of cardiopulmonary bypass. Additionally, the surgeon does not need significant room inside the patient to connect the anastomotic stents of the invention to the target vessel. For, example, unlike sutured anastomoses which require significant access to the aorta for the surgeon to suture the graft vessel thereto, the anastomotic stents of the invention allow the proximal end of the graft vessel to be connected to any part of the aorta. All parts of the aorta are accessible to the large vessel stents of the invention, even when minimally invasive procedures are used. Consequently, the graft vessel may be connected to the descending aorta, so that the graft vessel would not be threatened by damage during a conventional sternotomy if a second operation is required at a later time.

The anastomotic stents of the invention provide a sutureless connection between a graft and a target vessel, while minimizing thrombosis or restenosis associated with the anastomosis. The anastomotic stents can be attached to the target vessel inside a patient remotely from outside the patient using specially designed applicators, so that the stents are particularly suitable for use in minimally invasive surgical procedures where access to the anastomosis site is limited. The stents of the invention allow the anastomosis to be performed very rapidly, with high reproducibility and reliability, and with or without the use of cardiopulmonary bypass.

These and other advantages of the invention will become more apparent from the following detailed description of the invention and the accompanying exemplary drawings.

BRIEF DESCRIPTION OF THE DRAWINGS

FIGS. 28A–28H are elevational views, partially in section, of the applicator, and large vessel stent and vessel penetrating member therein during connection of the large vessel stent to a target vessel.

DETAILED DESCRIPTION OF THE INVENTION

Figure 1:
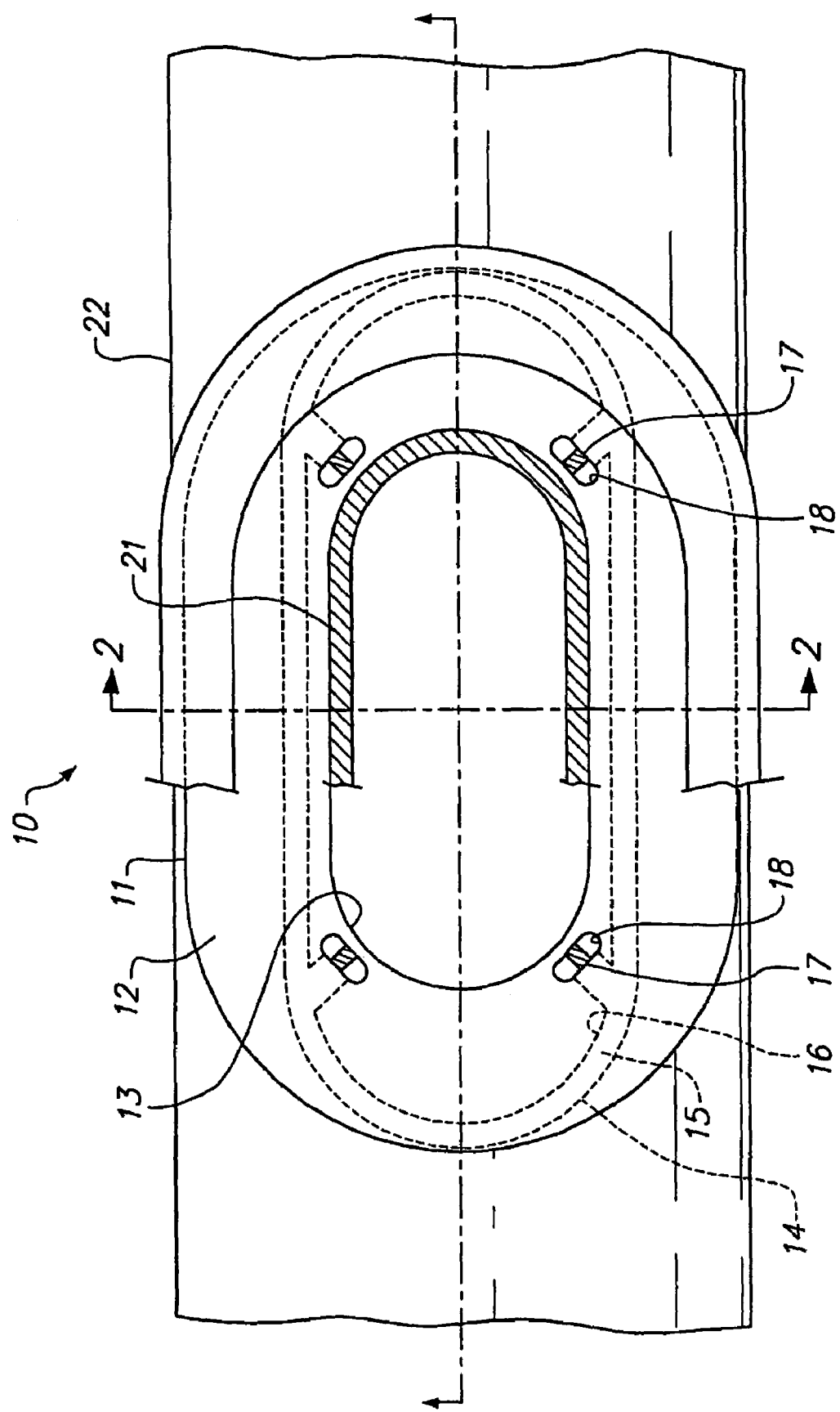
FIG. 1 is an elevational view, partially in phantom and in section, of a small vessel stent of the invention, with a graft vessel, partially in section and broken away, connected thereto, positioned in a target vessel.
Figure 2:
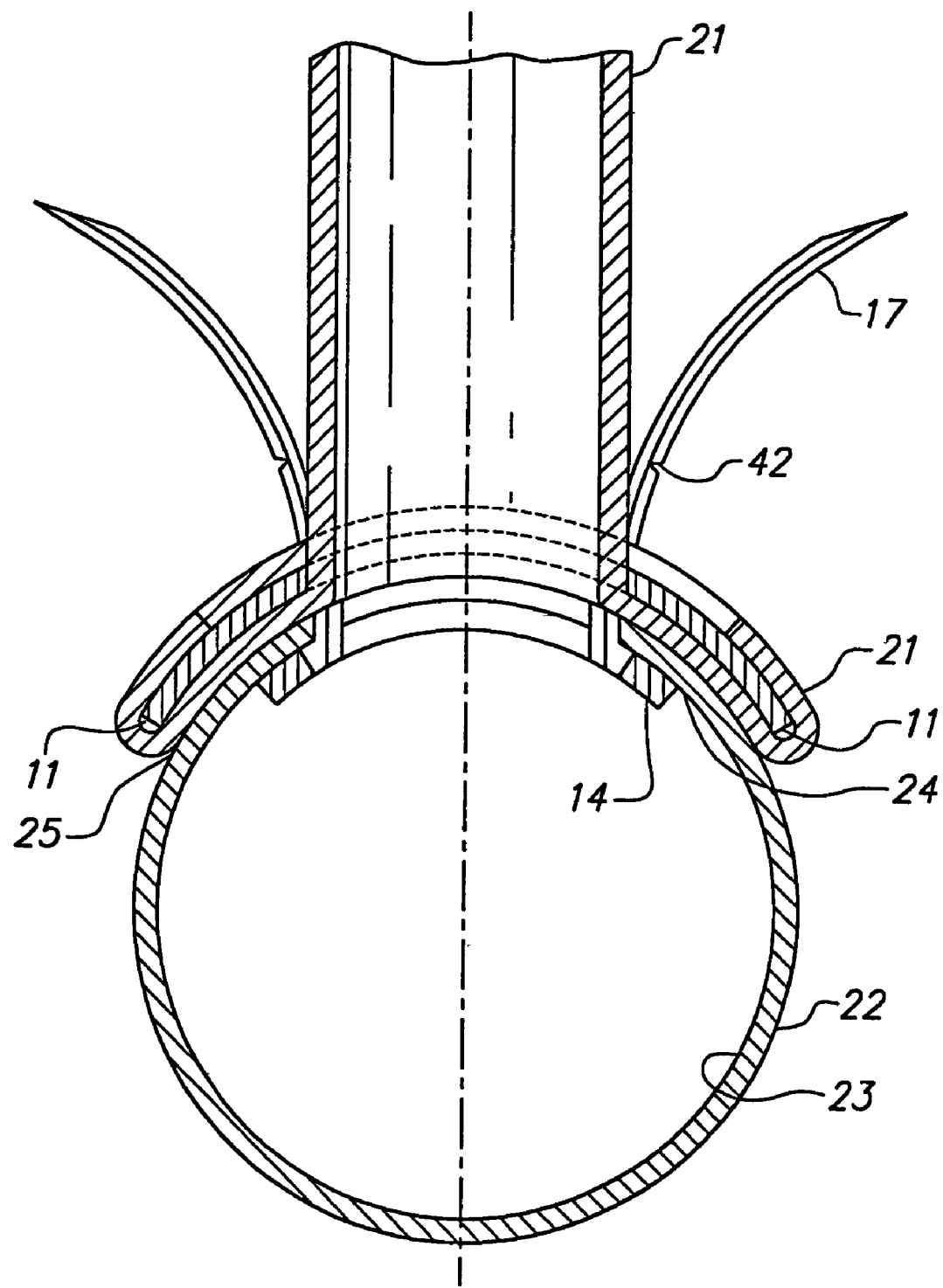
FIG. 2 is a transverse cross sectional view of the small vessel stent, together with the graft and target vessel, shown in FIG. 1, taken along lines 2—2.

A presently preferred embodiment of the small vessel stent 10 of the invention, for connecting one end of a graft vessel to a small target vessel, is illustrated in FIG. 1. The small vessel stent 10 comprises an outer flange 11 having a body 12 which defines an opening 13 configured to receive the end of the graft vessel 21, and an inner flange 14 having a body 15 which defines an opening 16. The inner flange is configured to be connected to the outer flange, with the openings 13, 16 at least in part aligned. In the embodiment illustrated in FIG. 1, prongs 17 on the inner flange are configured to be received within small openings 18 in the outer flange, to thereby connect the flanges together. As best illustrated in FIG. 2, showing a transverse cross section of the small vessel stent 10 shown in FIG. 1, taken along lines 2—2, the inner flange 14 is configured to be positioned within a lumen 23 of the target vessel 22 against an inner surface 24 of the target vessel, and the outer flange 11 is configured to be positioned against an outer surface 25 of the target vessel 22. In the embodiment illustrated in FIGS. 1 and 2, the inner and outer flanges have an arced configuration to facilitate positioning against the arced surface of the tubular vessel. The small vessel stent 10 is preferably used with small target vessels, such as arteries, which typically have thin walls and small inner diameters.

In the embodiment illustrated in FIG. 1, the inner and outer flanges have a short dimension and a long dimension, i.e. are substantially oblong. The graft receiving opening 13 in the outer flange, and the opening 16 in the inner flange, are also substantially oblong.

Figure 3:
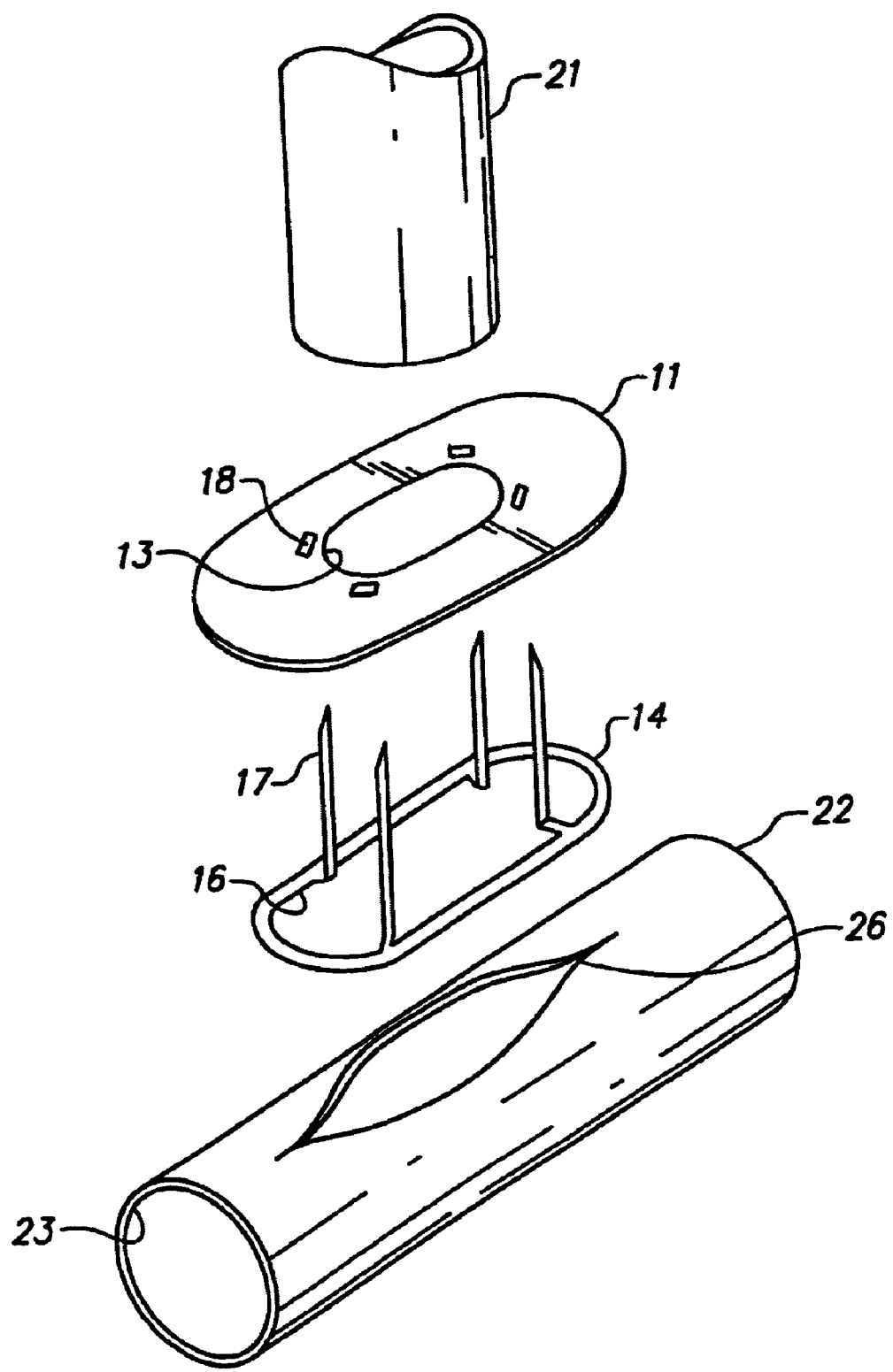
FIG. 3 is an exploded view of the graft vessel, the small vessel stent with the inner and outer flanges, and the graft vessel disconnected.
Figure 4:
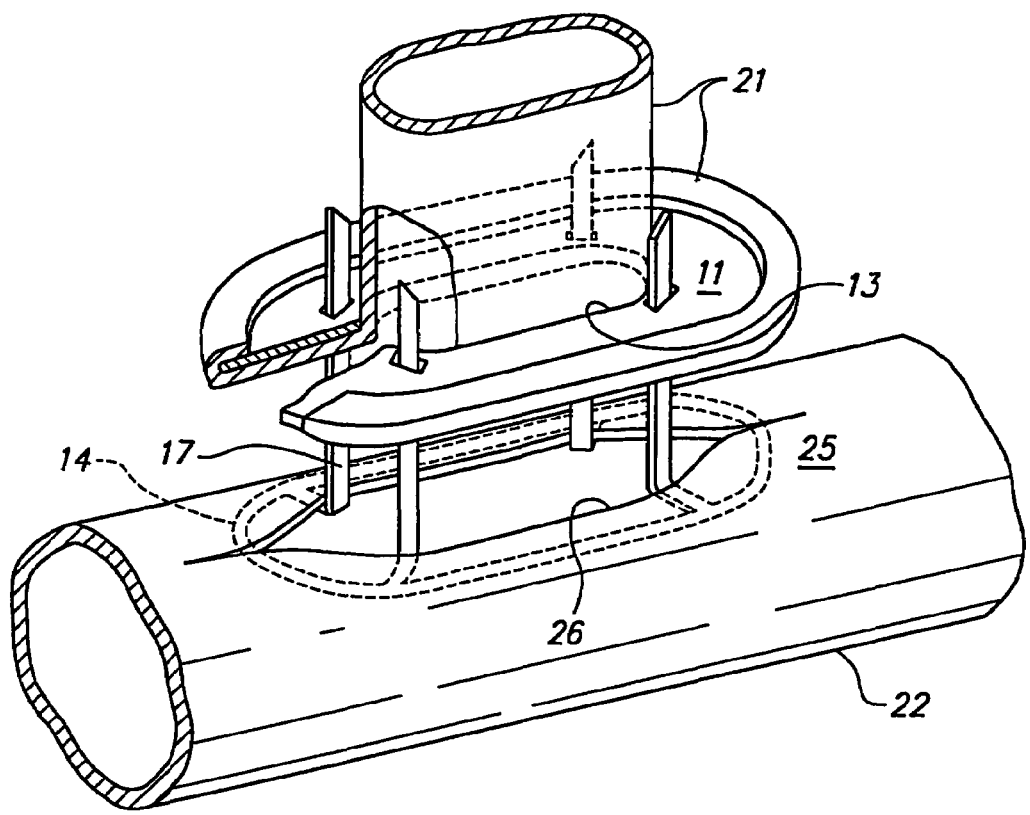
FIG. 4. is an elevational view, partially in phantom, of the small vessel stent shown in FIG. 3, with the outer flange and the graft vessel, partially broken away, connected thereto, and with the inner flange in the target vessel lumen.

FIG. 3 is an exploded view of the inner flange 14, outer flange 11, and a graft vessel 21, at an incision 26 in the target vessel 22. In FIG. 4, the graft vessel has been connected to the outer flange by inserting the end of the graft vessel through the graft receiving opening 13, and everting the graft end over the outer flange. Additionally, connecting members such as sutures, hooks or clips may be used to fix the graft vessel to the outer tubular member (not shown). The prongs 17 on the inner flange pierce through the wall of the graft vessel and then through the small openings 18 in the outer flange. FIG. 4 illustrates the inner and outer flanges loosely connected together for positioning at the target vessel, with only a partial length of the prongs 17 inserted through the prong receiving opening 18, before the flanges are tightened down around the wall of the target vessel.

Figure 5:
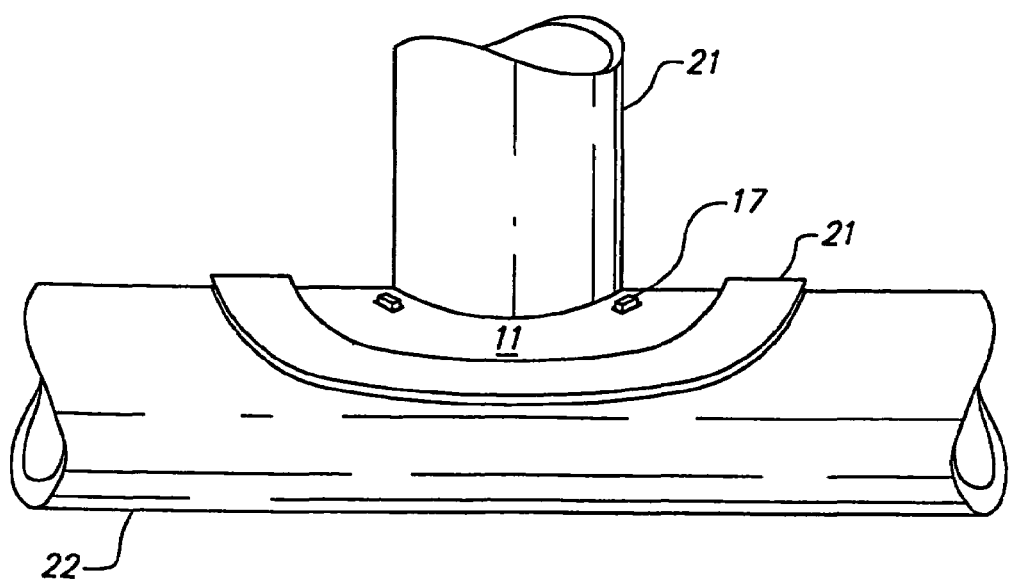
FIG. 5 is an elevational view of the small vessel stent shown in FIG. 4, connected to the target vessel.

With the outer flange 11 connected to the graft vessel 21 and the inner flange 14 connected to the outer flange 11, the inner flange is introduced into the incision 26 in the target vessel 22, and the inner and outer flanges are tightened together so that a compressive force is applied to the graft vessel against the outer surface 25 of the target vessel. Thus, the anastomosis channel is formed from the target vessel lumen, through opening in the inner flange, and into the graft vessel lumen. After the inner and outer flanges are tightened around the wall of the target vessel, in the embodiment having prongs 17, a length of the prongs extending above the target vessel can be broken off or otherwise removed. FIG. 5 is an elevational view of the small vessel stent shown in FIG. 4, connected to the target vessel, with a length of the free ends of the prongs 17 removed.

Figure 6:
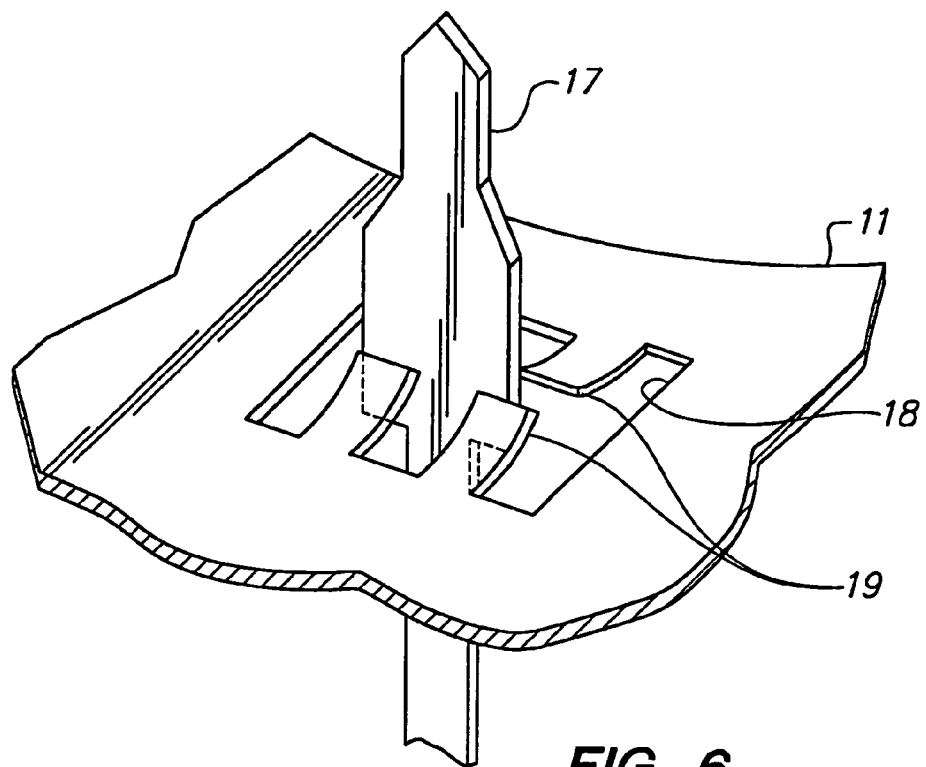
FIG. 6 is an elevational view of a prong and a prong receiving opening, on the outer flange which embodies features of the invention.

In one embodiment of the invention, the prongs 17 on the inner flange and the prong receiving openings 18 on the outer flange are configured to fixedly mate together. FIG. 6 illustrates one embodiment of the prong 17 and prong receiving openings 18. The opening 18 has deflectable tabs 19 which deflect to allow displacement of the prong 17 longitudinally into the opening from the under side of the outer flange to the upper side of the outer flange, but which wedge against the prong to prevent the inserted prong from moving out of the opening 18 from the upper side to the under side of the outer flange. Additionally, a quick release (not shown) may be provided on the prongs to allow the prongs which are only partially inserted through the prong receiving opening to be quickly released therefrom in the event of an aborted procedure.

Figure 7:
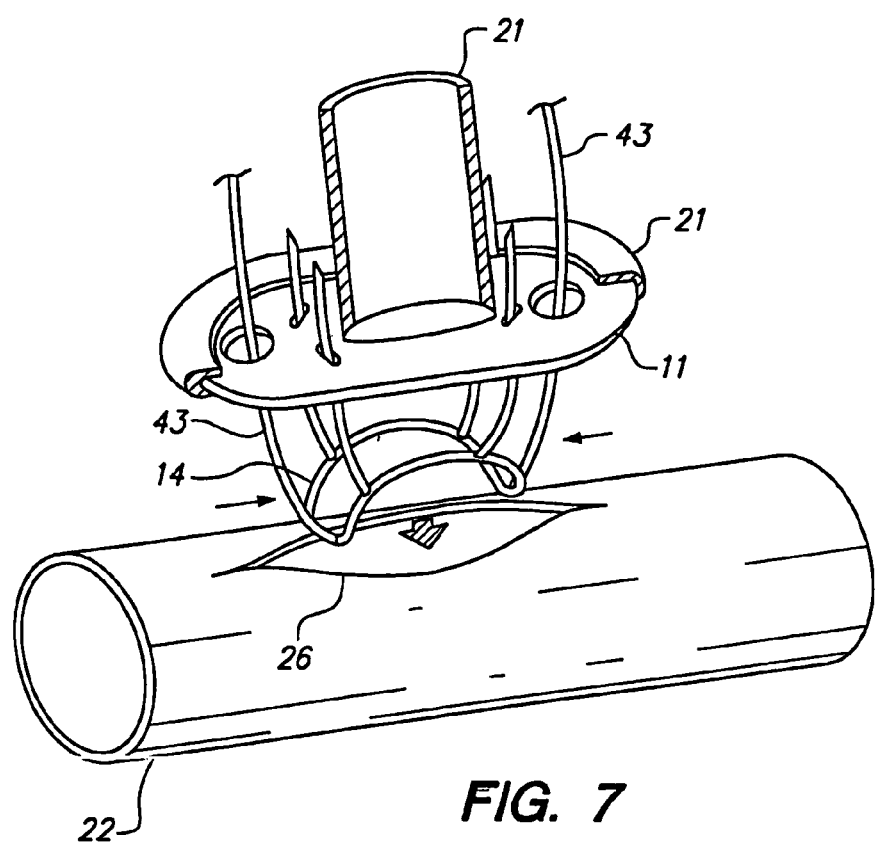
FIG. 7 is an elevational view, partially in section, of a small vessel stent with the inner flange folded for insertion into the target vessel, with the short dimension sides folded inward, and with the graft vessel, partially broken away.
Figure 8:
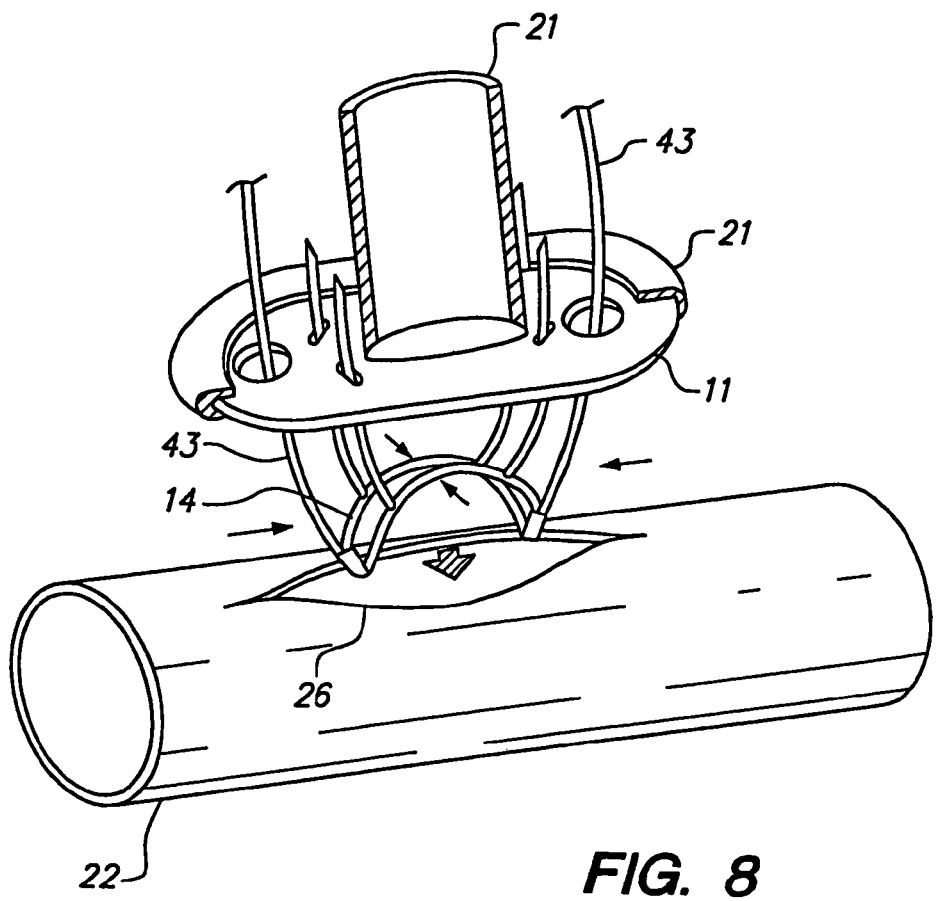
FIG. 8 is an elevational view, partially in section, of a small vessel stent with the inner flange folded for insertion into the target vessel, with the short dimension sides and the long dimension sides folded inward, and with the graft vessel, partially broken away.
Figure 9:
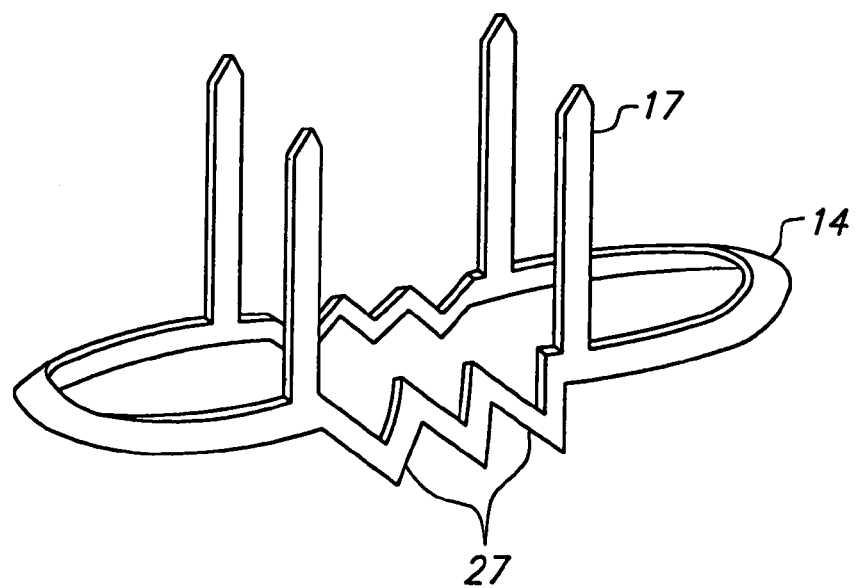
FIG. 9 is an elevational view of an compressible small vessel stent inner flange in a partially compressed configuration.

In a presently preferred embodiment of the small vessel stent, the inner flange has a folded configuration having a reduced profile to facilitate insertion into the incision in the target vessel. In one embodiment, the length of the stent is shortened by flexing the short dimensioned sides of the stent together, as illustrated in FIG. 7. To hold the inner flange in the folded configuration for insertion into the target vessel, a pair of inwardly tensioned arms 43, preferably as a part of an applicator, are used in one embodiment of the invention. Additionally, the width of the stent can be shortened by flexing the long dimensioned sides of the stent together, as illustrated in FIG. 8. In the presently preferred embodiment of the folding inner flange illustrated in FIGS. 7 and 8, the inner flange is formed from a superelastic or pseudoelastic material, such as a NiTi alloy, to facilitate folding the inner flange and to provide improved sealing against the wall of the target vessel after the inner flange is unfolded inside the target vessel lumen. However, other configurations may be used, as for example, an inner flange having a collapsible section. For example, FIG. 9 illustrates an inner flange having a collapsible section 27 on the long dimensioned sides of the inner flange, comprising a series of short turns in alternating directions. In FIG. 9, the collapsible section 27 is shown in a partially collapsed configuration in which the length of the inner flange is shortened by collapsing the long dimensioned sides of the inner flange. In a presently preferred embodiment, the inner flange having a collapsible section 27 is formed of stainless steel.

Figure 10:
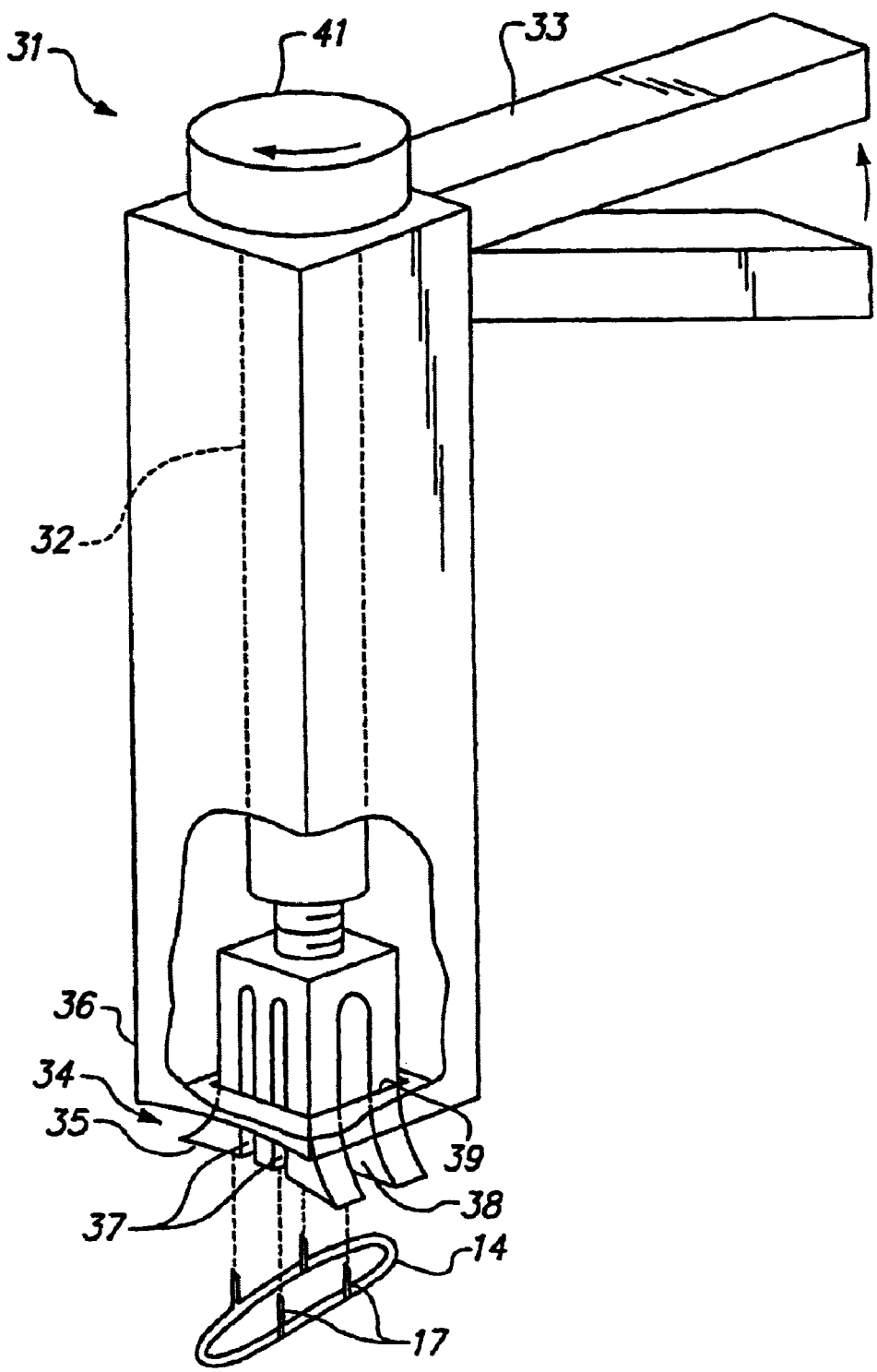
FIG. 10 is an elevational view, partially in section, of a small vessel stent applicator which embodies features of the invention.
Figure 11:
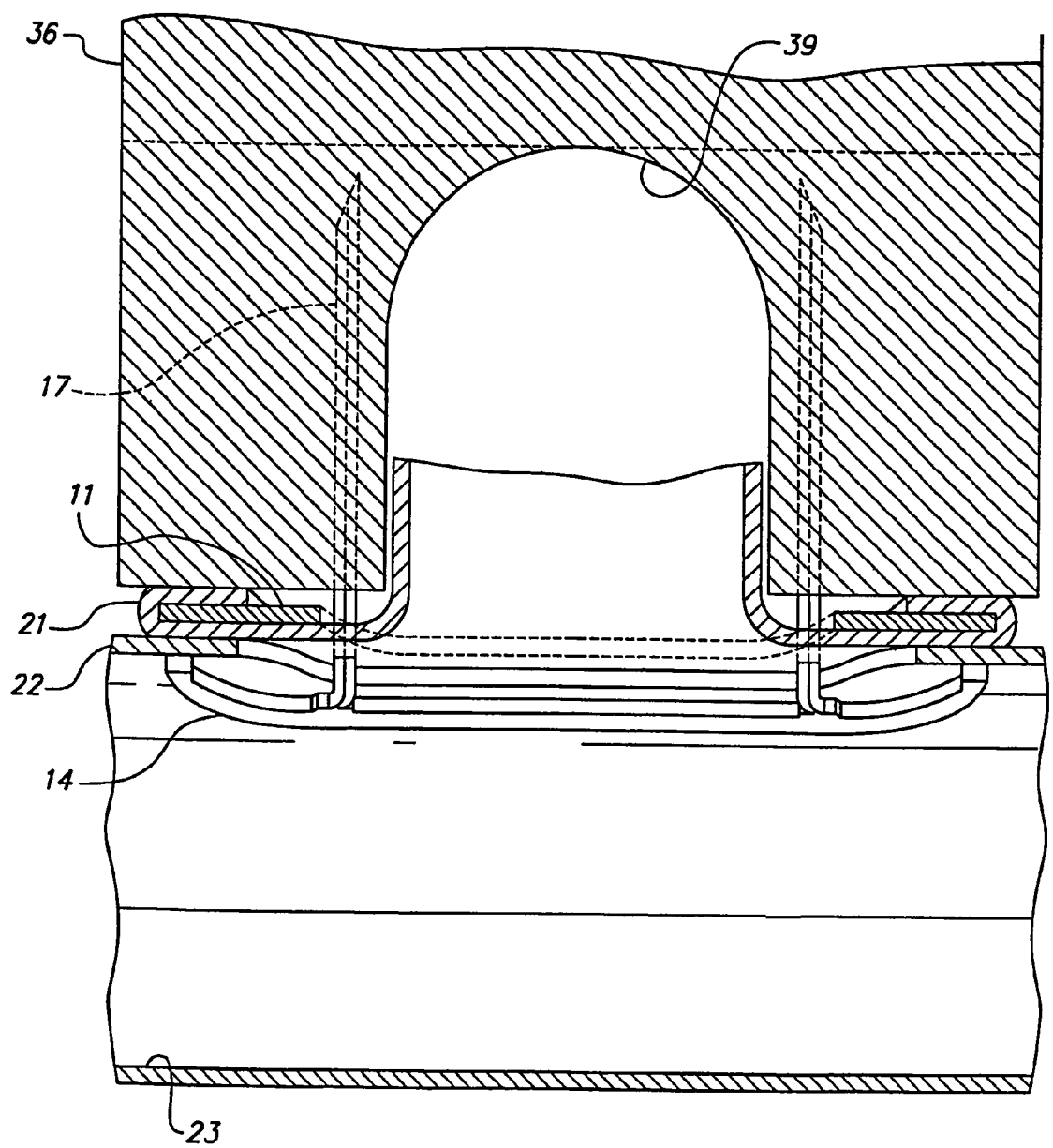
FIG. 11 is a longitudinal cross sectional view of the applicator shown in FIG. 10 with a small vessel stent therein, in position in a target vessel.

FIG. 10 illustrates an applicator 31 used to position the inner flange 14 within the target vessel lumen 23, and tighten the inner and outer flanges together around the wall of the target vessel. The applicator 31 generally comprises a shaft 32 with proximal and distal ends, a handle 33 on the proximal end, and a connecting member 34 on the distal end for releasably attaching to the small vessel stent. In the embodiment illustrated in FIG. 9, the connecting member 34 comprises an inner compressible member 35 which is slidably insertable into an outer housing member 36. The compressible member 35 has slots 37 configured to receive the prongs 17 on the inner flange 14, and an opening 38 configured to receive the graft vessel. The free end of the graft vessel, unconnected to the small vessel stent 10, is outside of the applicator via the opening 38. The housing member 36 has an inner chamber 39 configured to receive the compressible member 35. The chamber 39 is smaller than at least a section of the compressible member 35, to thereby compress the compressible member 35 to a smaller dimension when it is positioned within the chamber 39. The small vessel stent is releasably connected to the applicator, after the inner and outer flange together with a graft vessel are connected together, by inserting the prongs 17 on the inner flange into the slots 37. The compressible member 35 clamps onto the prongs 17 as the compressible member 35 is positioned within the chamber 39 and the slots 37 are thereby compressed. In the embodiment illustrated in FIG. 10, the compressible member 35 is partially out of the housing. Additionally, a connecting member (not shown)

such as a clasp, clamp, or hook on the distal end of the applicator may be used to connect the outer flange to the applicator. FIG. 10 illustrates, in an exploded view, the positioning of the inner flange 14 for releasably connecting to the applicator. Of course, as discussed above, the inner flange 14 is typically connected to the outer flange with a graft vessel attached thereto before being connected to the applicator. The applicator is then used to position the stent in place at the incision in the target vessel, with the inner flange inside the target vessel lumen and the outer flange against the outer surface of the target vessel. To release the small vessel stent 10 from the applicator, the compressible member 35 is displaced out of the housing member 36, so that the prongs 17 are released from the slots 37 as the slots expand. In the embodiment illustrated in FIG. 10, the applicator has a knob 41 for turning the shaft 32 to draw the compressible member 35 up into the chamber 39. The handle 33 may be used to deploy the small vessel stent by squeezing the handle together to displace the compressible member 35 and housing member 36 relative to one another. FIG. 11 is a longitudinal cross sectional view of an applicator as shown in FIG. 10, with a small vessel stent therein, in position at a target vessel.

In addition, the applicator 31 may be provided with a insertion member for holding the inner flange in the folded configuration facilitating introduction into the target vessel lumen through the incision in the target vessel. In one embodiment, the applicator insertion member comprises a pair of inwardly tensioned arms 43 extending past the distal end of the shaft for releasably holding the inner flange in the folded configuration, as illustrated in FIGS. 7 and 8.

In the method of the invention, the small vessel stent connects one end of a graft vessel to a target vessel to form an anastomosis. The target vessel is incised, and balloons on occlusion catheters positioned against the target vessel are inflated to occlude blood flow upstream and downstream of the anastomosis site. The outer flange is attached to one end of a graft vessel as described above, and, in the embodiment illustrated in FIG. 1, the prongs on the inner flange are inserted through the graft vessel and into the prong receiving openings in the outer flange. The graft vessel may be occluded with a temporary clamp on the mid portion of the graft, to prevent blood loss through the graft vessel during the procedure. The inner flange is inserted into the target vessel lumen, and the inner and outer flanges are tightened together to compress the graft vessel against the outer surface of the target vessel. After the inner and outer flanges are tightened together, the free end of each prong is broken off to decrease the length of the prongs left inside the patient. The prongs are typically provided with a weakened point 42 near the body of the inner flange to facilitate breaking of the prong by tensile forces or by fatigue failure due to strain hardening. The occlusion balloons are deflated and the occlusion catheters removed, with the stent connected to the target vessel and the graft vessel in fluid communication with the target vessel lumen.

In the embodiment illustrated in FIG. 1, the outer flange is longer and wider than the inner flange. The outer flange has a length of about 4 mm to about 12 mm, preferably about 7 mm to about 9 mm, and a width of about 1 mm to about 5 mm. The wall thickness of the body of the outer flange is about 0.10 mm to about 0.30 mm. The inner flange has a length of about 4 mm to about 12 mm, preferably about 7 mm to about 9 mm, and a width of about 0.5 mm to about 5 mm, and preferably about 2 mm to about 4 mm. The wall thickness of the body of the inner flange is about 0.10 mm to about 0.25 mm. The inner and outer flanges are preferably formed of stainless steel, preferably 316 stainless steel, although, as previously discussed herein, superelastic or pseudoelastic materials such as nickel titanium alloys, titanium, or tantalum, may also be used. Additionally, advanced polymers which can be plastically deformed, such as polyetheretherketone, may be used.

Figure 12:
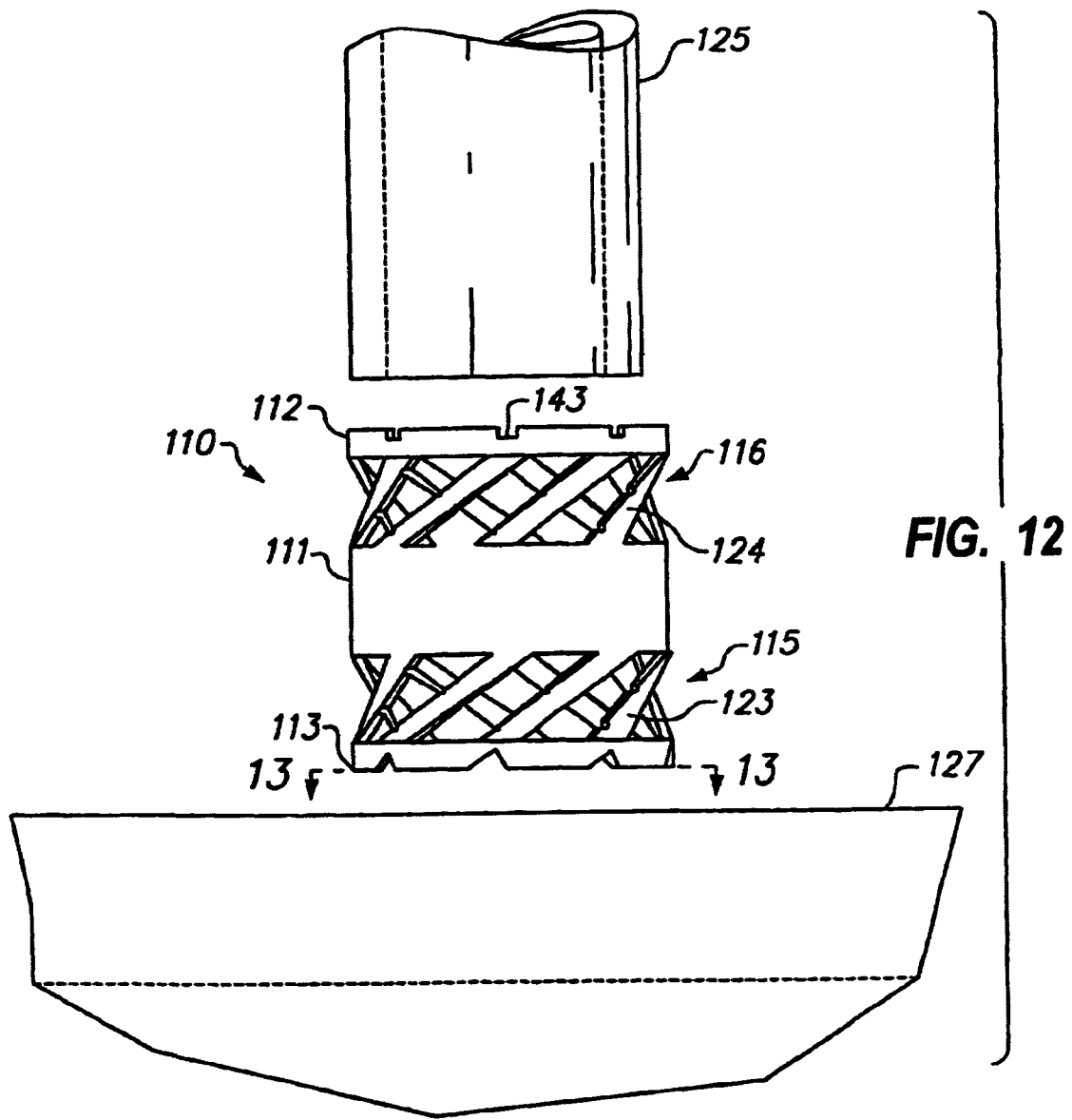
FIG. 12 is an elevational, exploded view of a graft vessel, a large vessel anastomotic stent of the invention with the deformable sections in the first configuration, and a target vessel.
Figure 13:
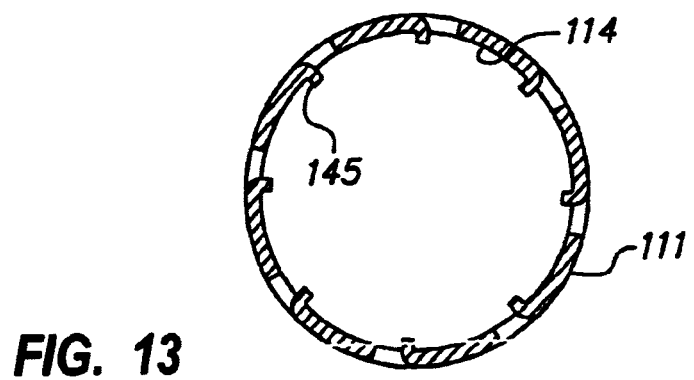
FIG. 13 is a transverse cross sectional view of the large vessel stent shown in FIG. 12, taken along lines 13—13.
Figure 14:
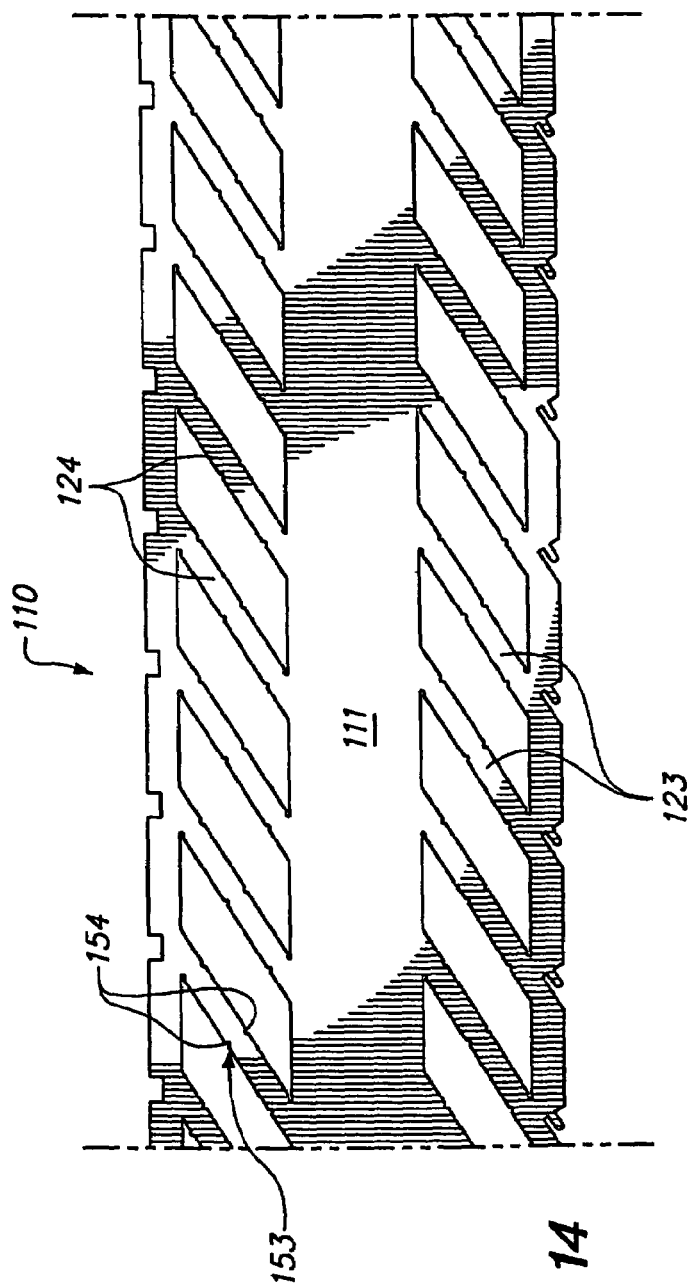
FIG. 14 is an flattened view of a large vessel anastomotic stent of the invention with the deformable sections in the first configuration.

FIG. 12 illustrates a presently preferred embodiment of the large vessel stent 110 of the invention, for connecting one end of a graft vessel 125 to a large target vessel 127. The large vessel stent 110 comprises a substantially cylindrical body 111 having an open proximal end 112, open distal end 113, a lumen 114 extending therein configured to receive the end of the graft vessel 125. FIG. 13 illustrates a transverse cross section of the large vessel stent 110 shown in FIG. 12, taken along lines 13—13. FIG. 14 illustrates a flattened view of the large vessel stent 110 shown in FIG. 12.

Figure 16:
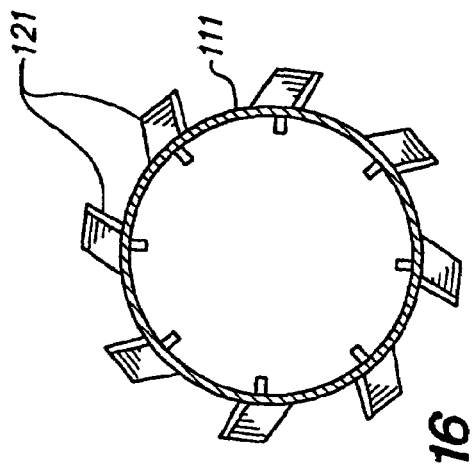
FIG. 16 is a transverse cross sectional view of the large vessel stent shown in FIG. 15, taken along lines 16—16.
Figure 15:
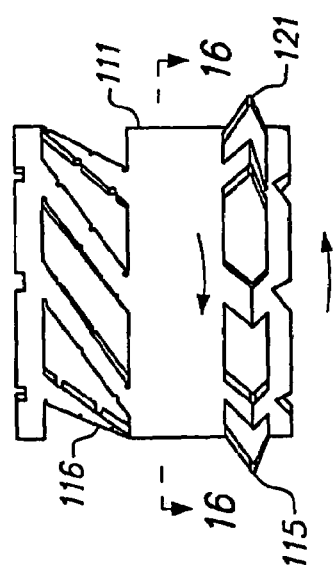
FIG. 15 is an elevational view of a large vessel anastomotic stent of the invention with the distal deformable section in the second configuration.
Figure 20:
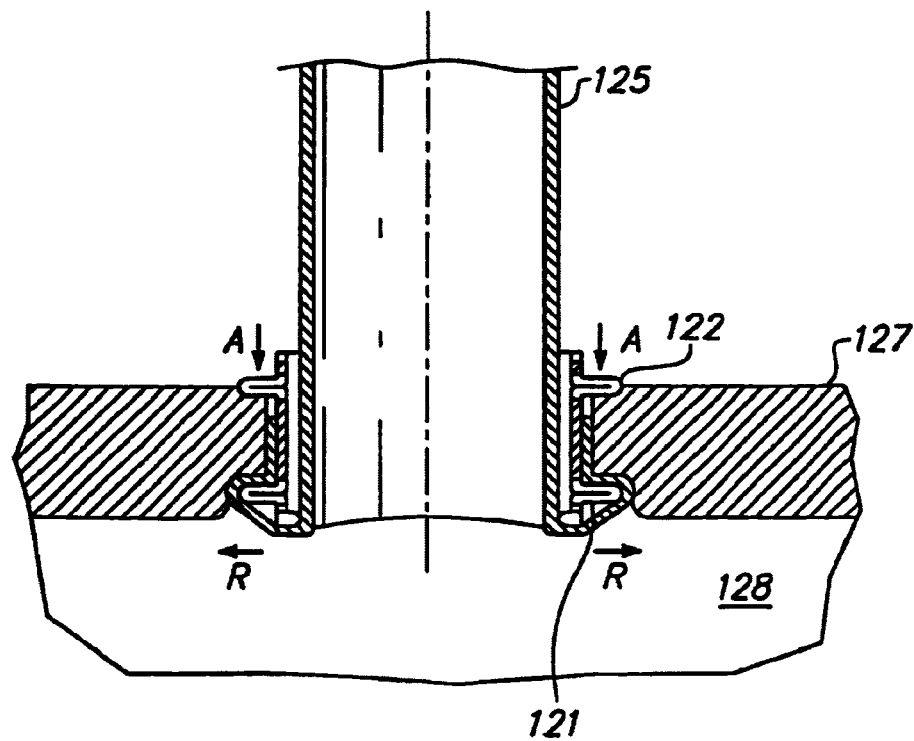
FIG. 20 is a longitudinal cross-sectional view of the large vessel stent shown in FIG. 19, with the proximal end deformable section in the second configuration.

The cylindrical body has a distal deformable section 115 and a proximal deformable section 116. The deformable sections 115, 116 have a first configuration for insertion into the target vessel, and a radially expanded second configuration for connecting to the target vessel. In the embodiment illustrated in FIG. 12, the distal and proximal deformable sections 115, 116 comprises a plurality of helical members 123, 124, respectively. In the embodiment illustrated in FIG. 12, each helical member has a proximal end radially spaced on the stent body relative to the helical member distal end. The helical members are radially spaced around the circumference of the cylindrical body between longitudinally spaced portions of the cylindrical body. In FIG. 12, the helical members forming the deformable sections are shown in the first configuration prior to being radially expanded to the second configuration. As illustrated in FIG. 15, the distal deformable section 115 radially expands to the second configuration to form a distal end flange 121, configured to apply a force radial to the cylindrical body 111 longitudinal axis against the target vessel and thereby connect the stent to the target vessel. Similarly, the proximal deformable section 116 radially expands to the second configuration to form a proximal end flange 122, as illustrated in FIG. 20. The flanges 121, 122 are deployed by circumferentially rotating the proximal end of the stent body relative to the distal end of the stent body. Such rotation causes the stent body to longitudinally collapse as the helical members radially expand from the first to the second configuration. FIG. 16 illustrates a transverse cross section of the large vessel stent 110 shown in FIG. 15, taken along lines 16—16.

Figure 17:
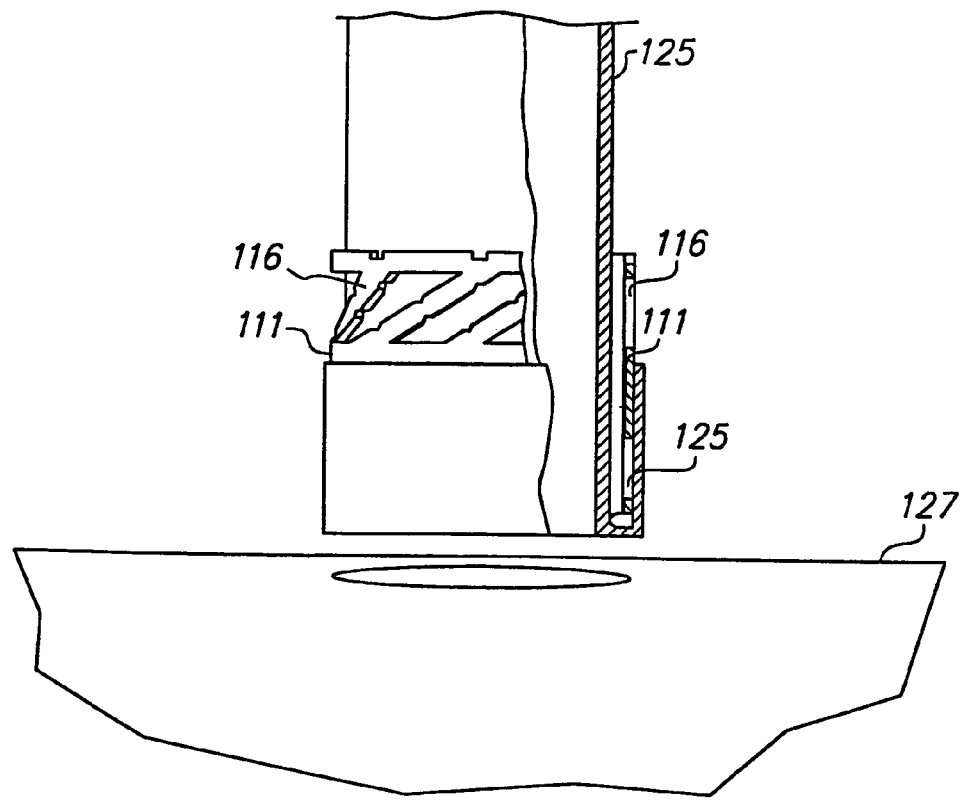
FIG. 17 is an elevational view, partially in section and broken away, of the large vessel stent shown in FIG. 12, with an everted graft vessel thereon, and a target vessel.

FIG. 17 illustrates the large vessel stent shown in FIG. 12 with a graft vessel 125 attached thereto. The graft vessel is attached to the large vessel anastomotic stent by inserting one end of the graft vessel into the proximal end of the cylindrical body and, in a preferred embodiment, everting the graft end 126 out the cylindrical body distal end. The graft vessel may be everted over all or only a section of the outer surface of the large vessel stent 110. In the embodiment illustrated in FIG. 17, the graft is everted over the distal deformable section 115 which is in the first configuration prior to being radially expanded to the second configuration.

Figure 18:
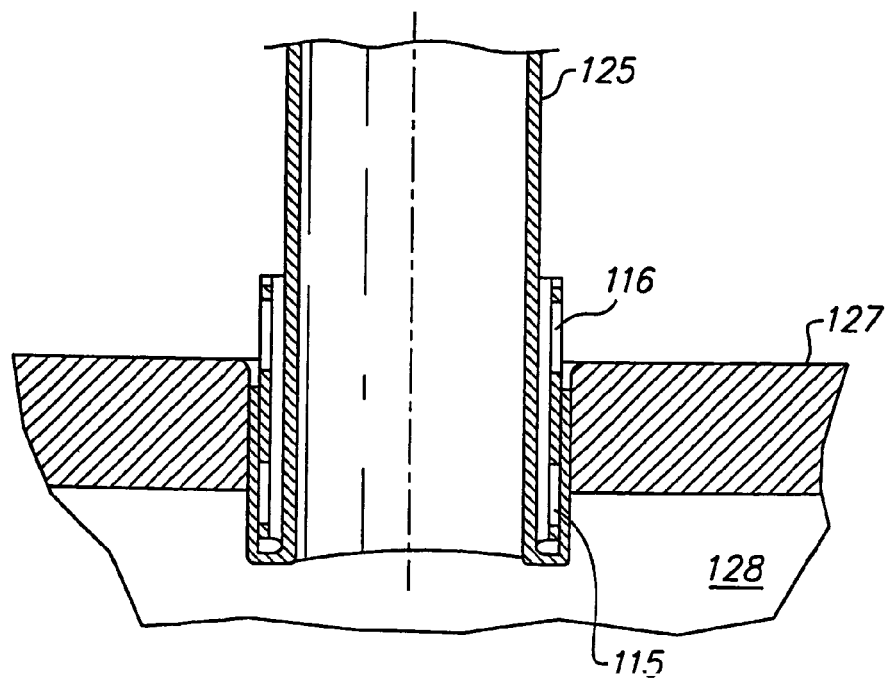
FIG. 18 is a longitudinal cross-sectional view of the large vessel stent and graft vessel thereon in a target vessel.
Figure 19:
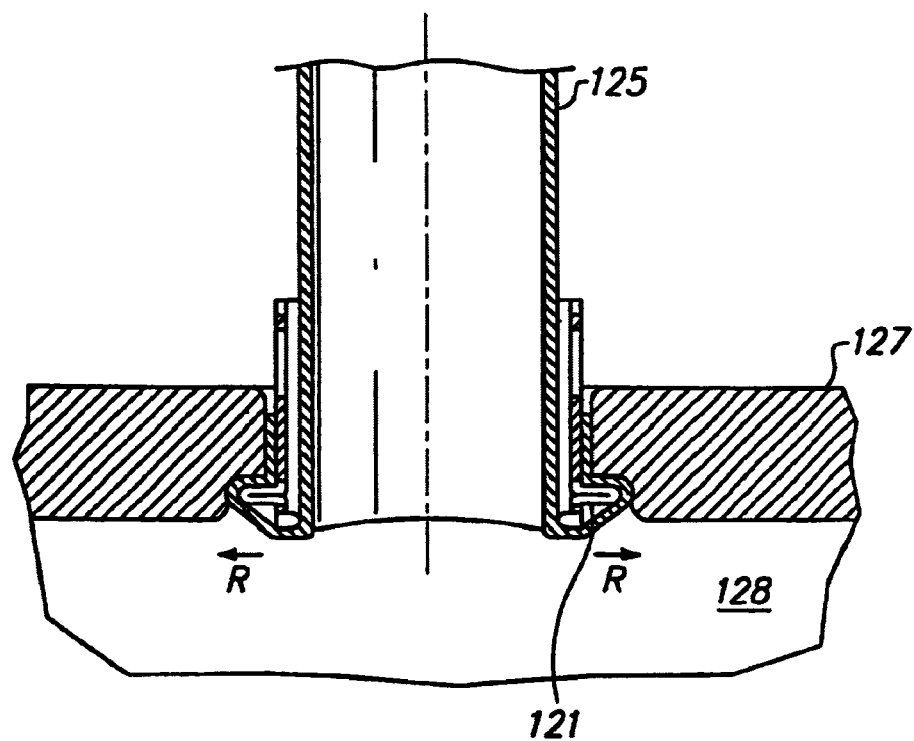
FIG. 19 is a longitudinal cross-sectional view of the large vessel stent shown in FIG. 18, with the distal end deformable section in the second configuration.

FIGS. 18–20 illustrate the large vessel stent shown in FIG. 17 within a wall of the target vessel 127 before and after deployment of the distal flange 121 and proximal flange 122. In FIG. 18, the stent has been inserted into an incision in a wall of the target vessel, with the distal end of the stent within the lumen 128 of the target vessel 127 and the proximal end 112 of the stent extending outside of the target vessel. In FIG. 19, the distal deformable section 115 has been radially expanded to form the distal end flange 121. During deployment of the distal end flange, the stent body longitudinally collapses, and the distal end flange is positioned at least in part within the wall of the target vessel, so that the flange applies a force radial to the stent longitudinal axis, illustrated by the arrow R, against the wall of the target vessel defining the incision therein. Additionally, an axial force, illustrated by the arrow A, is applied against the target vessel wall, compressing the target vessel wall. The final position of the distal end flange may vary, with the distal end flange being completely within the target vessel wall as shown, or, alternatively, partially within the target vessel lumen (not shown). In FIG. 20, the proximal deformable section 116 has been radially expanded to form the proximal end flange 122. The proximal end flange positioned against the outer wall of the target vessel produces an axial force, illustrated by the arrow A, against the target vessel. In the embodiment illustrated in FIG. 20, the proximal end flange is in contact with an outer surface of the target vessel wall. Alternatively, the proximal end flange may be in contact with the media of the target vessel between the inner and outer surface of the target vessel wall, and preferably with the proximal end of the stent flush with the outer surface of the target vessel (not shown). The degree to which flange is deployed may be varied to control how and where the flange contacts the target vessel wall. Thus, depending on the thickness of the target vessel wall, the proximal deformable section can be radially expanded and longitudinally collapsed to a greater or lesser degree, so that the proximal end flange is in contact with the target vessel either on an outer surface of the target vessel or within the incision therein in contact with the media of the target vessel wall.

Although the large vessel stent 110 is shown in FIG. 12 with a proximal deformable section and a distal deformable section, forming proximal and distal flanges, respectively, the large vessel stent may have one or more deformable sections. For example, an intermediate deformable section (not shown) between the proximal and distal end deformable sections may be provided for additional sealing and securing force against the media of the target vessel wall.

Figure 21:
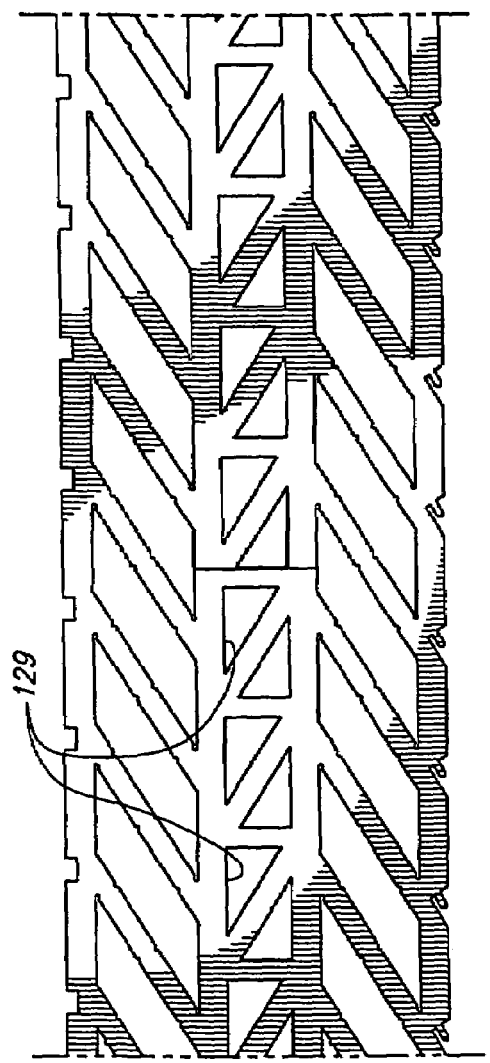
FIG. 21 is a flattened view of an alternative embodiment of the large vessel anastomotic stent of the invention having voids in the body.
Figure 22:
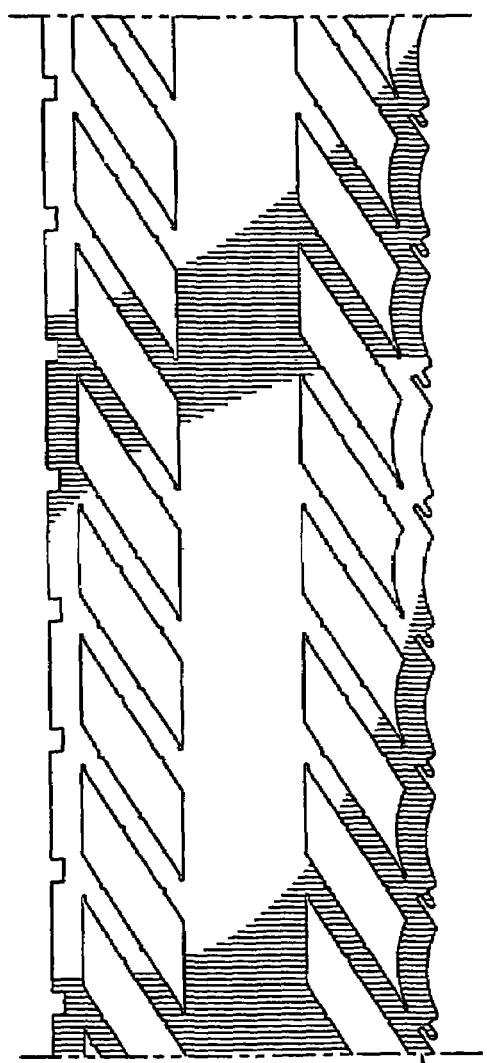
FIG. 22 is a flattened view of an alternative embodiment of the large vessel anastomotic stent of the invention having a curvilinear distal end.

In the large vessel stent illustrated in FIG. 12, the intermediate section of the body is solid. FIG. 21 illustrates an alternative embodiment in which voids or openings 129 are provided in the body wall which allow for tissue ingrowth, to thus facilitate sealing and securing of the anastomosis. In another embodiment of the large vessel stent, illustrated in FIG. 22, a peripheral edge on the distal end of the large vessel stent is curvilinear, so that deployment of the distal end flange increases the diameter of the open distal end. The generally sinusodial edge increases the diameter of the opening in the distal end as the distal deformable section 115 is longitudinally collapsed.

Figure 23:
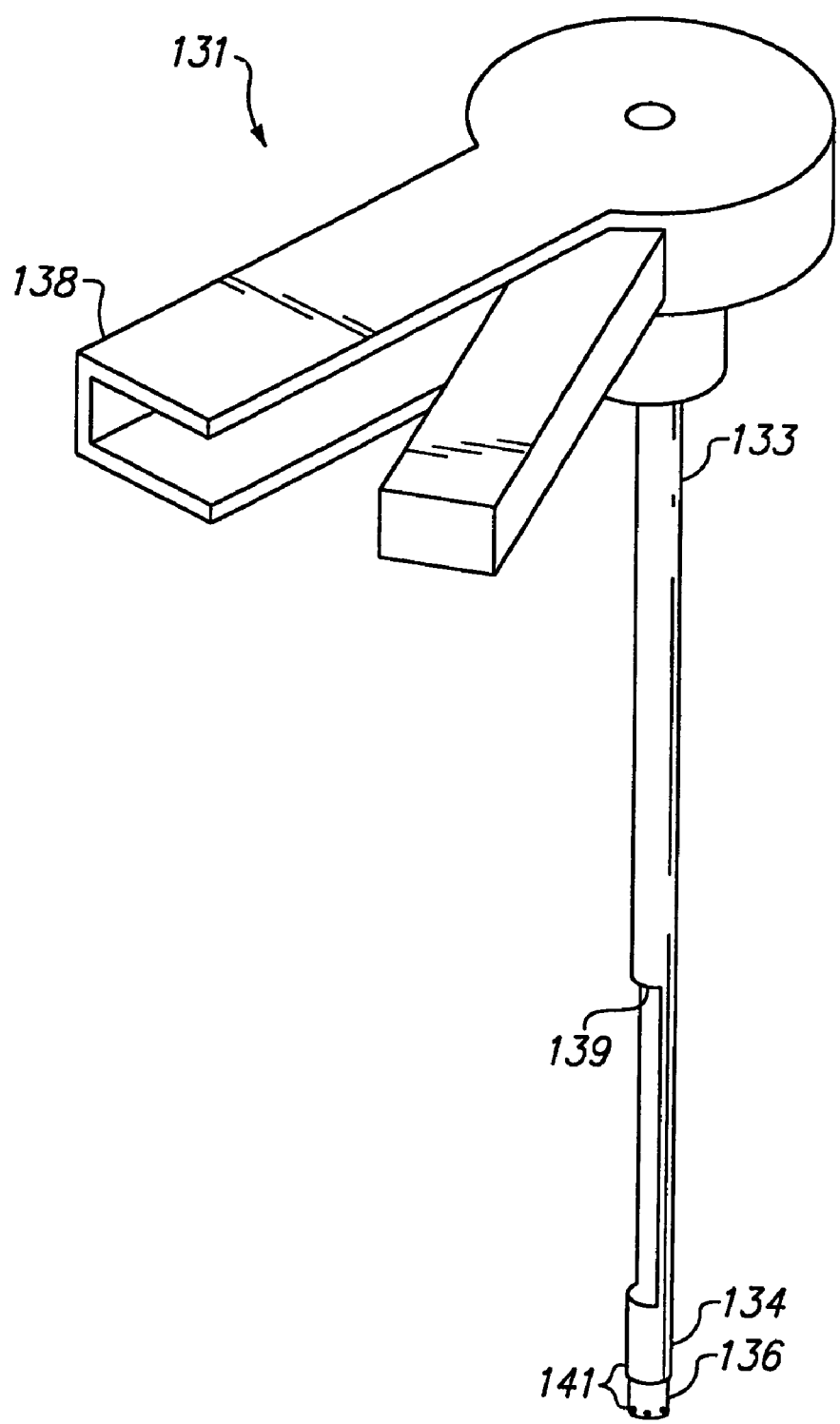
FIG. 23 is an elevational view of a large vessel stent applicator which embodies features of the invention.
Figure 24:
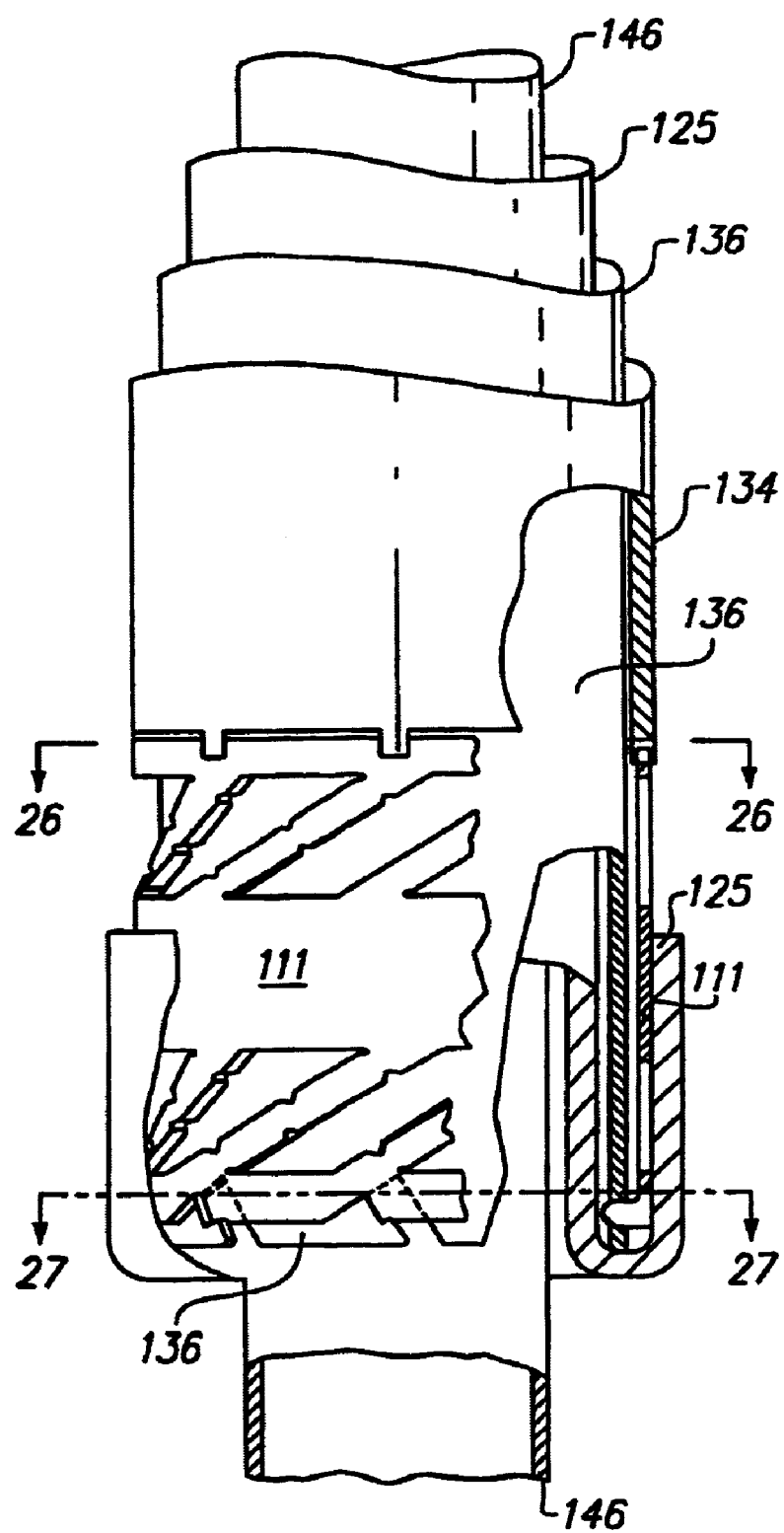
FIG. 24 is a transverse cross sectional view, partially in section and broken away of the distal end of an applicator with a large vessel stent and graft vessel thereon, with a vessel penetrating member therein.
Figure 25:
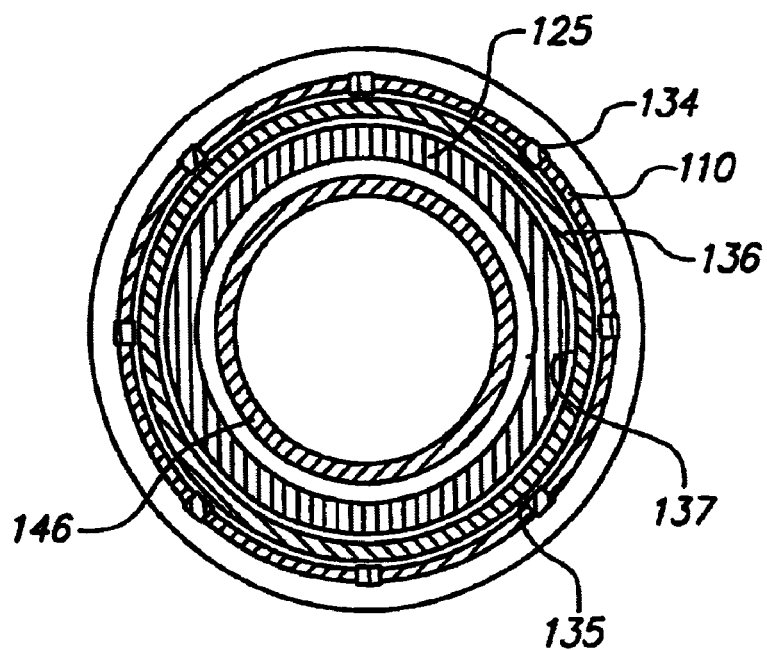
FIGS. 25 and 26 are transverse cross sectional views of the applicator assembly shown in FIG. 24 taken along lines 25—25 and 26—26, respectively.
Figure 26:
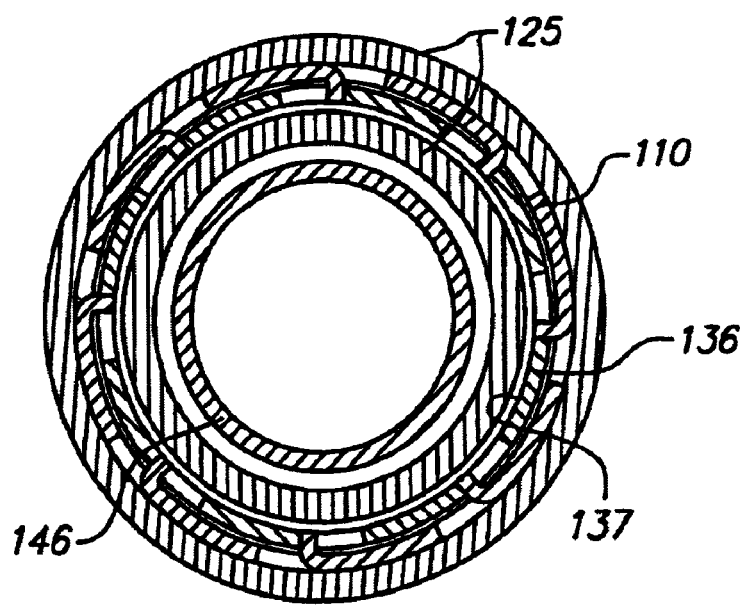
Figure 27:
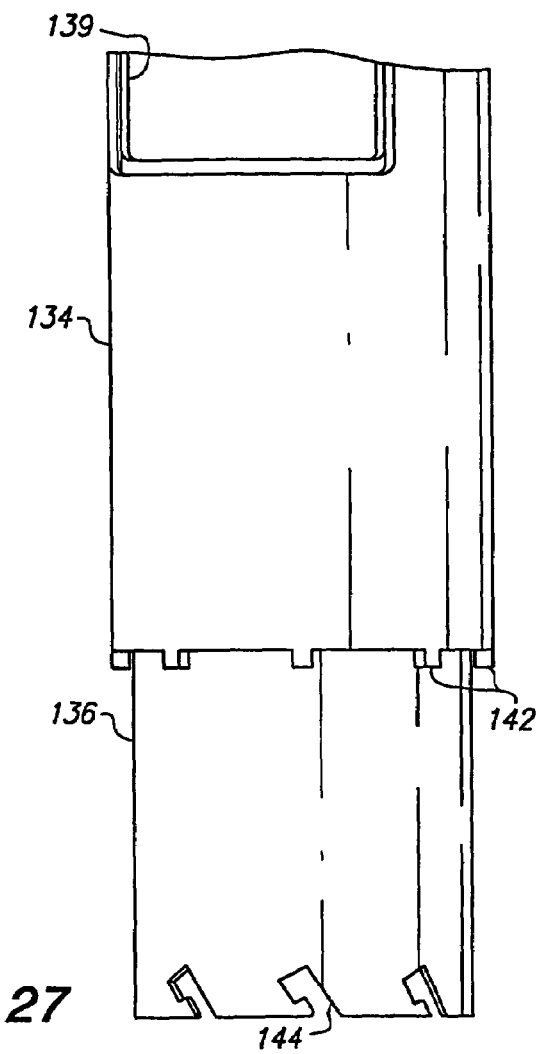
FIG. 27 is an elevational view of the distal end of the applicator shown in FIG. 23.

An applicator 131 is typically used to deploy the flanges and connect the large vessel stent 110 to the target vessel 127, as illustrated in FIG. 23. In the embodiment illustrated in FIG. 23, the applicator 131 comprises an elongated stent delivery member comprising a shaft 133 having an outer tubular member 134 having a lumen 135 therein, an inner tubular member 136 having a lumen 137 configured to receive the graft vessel 125 and being rotatably located within the lumen of the outer tubular member, a handle 138 on the proximal end of the shaft, and connecting members 141 on the distal end of the inner and outer tubular members which releasably secure the large vessel stent 110 to the applicator 131. The distal and proximal ends of the large vessel stent 110 releasably secure to the inner and outer tubular members, respectively, and the inner and outer tubular members are rotatable relative to one another, so that the distal end of the stent can be rotated relative to the proximal end of the stent and the flanges thereby deployed. In the embodiment illustrated in FIG. 23, longitudinal openings 139, preferably coextensive with one another, in the inner and outer tubular members are provided to facilitate positioning the graft vessel, and large vessel stent connected thereto, on the applicator 131. FIG. 24 illustrates an enlarged view of the distal end of an applicator as shown in FIG. 23, with a large vessel stent 110 and graft vessel 125 thereon. FIGS. 26 and 27 illustrate transverse cross sections of the applicator shown in FIG. 24, taken along lines 26—26 and 27—27, respectively.

FIG. 27 illustrates an enlarged view of the distal end of the applicator 131 shown in FIG. 23. In the embodiment illustrated in FIG. 27, the connecting members 141 on the outer tubular member 134 comprise tabs 142 configured to mate with slits 143, as illustrated in FIG. 12, on the proximal end of the stent. The connecting members 141 on the inner tubular member 136 comprise angular slits 144 which slidably receive tabs 145, as illustrated in FIG. 13 on the distal end of the stent. The tabs on the distal end of the stent are introduced into the slits on the applicator inner tubular member and a slight twisting motion releasably secures the tabs therein. A variety of suitable connection members can be used including releasable clamps, clips, hooks, and the like.

In one embodiment of the invention, the applicator 131 includes a vessel penetrating member 146, as illustrated in FIGS. 24 and 28, for forming an incision in the target vessel. Additionally, the applicator may be provided with one or more inflatable members for enlarging the incision, and/or drawing the applicator and stent into the incision. For example, in the embodiment shown in FIG. 28, a vessel penetrating member 146 having proximal and distal ends, a piercing member 147 on the distal end, and at least one inflatable member on a distal section of member 146, is configured to be received in the inner lumen of the inner tubular member 136. In the presently preferred embodiment illustrated in FIG. 28, a proximal balloon 148, which is preferably formed from noncompliant material, is provided on the outer tubular member for expanding the incision in the target vessel, and a distal balloon 151, which is preferably formed from compliant material, is provided distal to the noncompliant balloon 148, for drawing the vessel penetrating member 146 into the target vessel lumen 128. However, the distal balloon may be omitted and the catheter advanced through the incision and into the target vessel lumen physically or by other suitable methods, as when the proximal balloon is shaped to advance into the target vessel lumen during inflation. Additionally, the target vessel may be held to resist the force of inserting the stent into the aortal wall, as by a suction applicator (not shown) positioned against an outer surface of the target vessel, which pulls the target vessel toward the applicator.

In the method of the invention, the large vessel stent, with a graft vessel connected thereto, is introduced into the patient, inserted into the target vessel and connected thereto by deployment of the flange. FIGS. 28A–28H illustrate the connection of the large vessel stent to a target vessel. The stent 110, with an everted graft vessel 125 thereon, is releasably secured to the distal end of the applicator. The graft vessel is within the lumen of the inner tubular member, and the vessel penetrating member 146 is within the lumen of the graft vessel 125. As shown in FIG. 28A, the applicator 131 and stent 110 assembly is introduced into the patient and positioned adjacent the target vessel 127. An incision in the target vessel wall is formed by inserting the piercing member 147 into the target vessel, and the incision is enlarged by inflating the proximal balloon 148 on the vessel penetrating member 146, see FIGS. 28B and 28C. The distal end of the applicator is then displaced distally into the target vessel lumen 128 by inflating the distal balloon 151, see FIG. 28D. With the stent in position within the incision in the target vessel, the applicator inner tubular member is rotated relative to the applicator outer tubular member, so that the distal end of the stent rotates relative to the proximal end of the stent, and the distal end flange is deployed, see FIG. 28E. In the embodiment illustrated in FIG. 28D, the distal end of the stent is positioned within the target vessel lumen before the distal end flange 121 is deployed, to facilitate deployment thereof. In a presently preferred embodiment, the distal deformable section is positioned at least in part within the target vessel lumen before the distal flange is deployed. However, it is not required that the deformable sections are outside of the incision in the target vessel wall for the flanges to be deployed. The proximal end flange 122 is deployed by further rotating the applicator tubular members as outlined above for the distal end flange, see FIG. 28F. The balloons 148, 151 on the vessel penetrating member 146 are then deflated and the applicator 131 removed from the target vessel 127, leaving the graft vessel 125 connected thereto, see FIGS. 28G and 28H.

In a presently preferred embodiment, the distal end flange is configured to deploy at lower torque than the proximal end flange. A deflecting section 153 is provided on the helical members 123, 124, which bends during the deployment of the flanges. In one embodiment of the invention, illustrated in FIG. 14, the deflecting section 153 is formed by at least one notch in each helical member, having a depth which decreases the transverse dimension of the helical members at the notch. In the embodiment of the large vessel stent illustrated in FIG. 14, the a deflecting section is formed by two opposed notches 154 on opposite sides of the helical members. The notches on the distal helical members have a depth that is greater than the depth of the notches on the proximal helical members. Consequently, the transverse dimension of the deflecting section on the distal helical member is smaller than that of the proximal helical members, so that the distal flange will deploy before the proximal flange. Thus, the distal section helical members radially expand at lower torque than the proximal helical members, so that rotating the proximal and distal ends of the stent body relative to one another causes the distal end flange to deploy first, followed by the proximal end flange.

Figure 29:
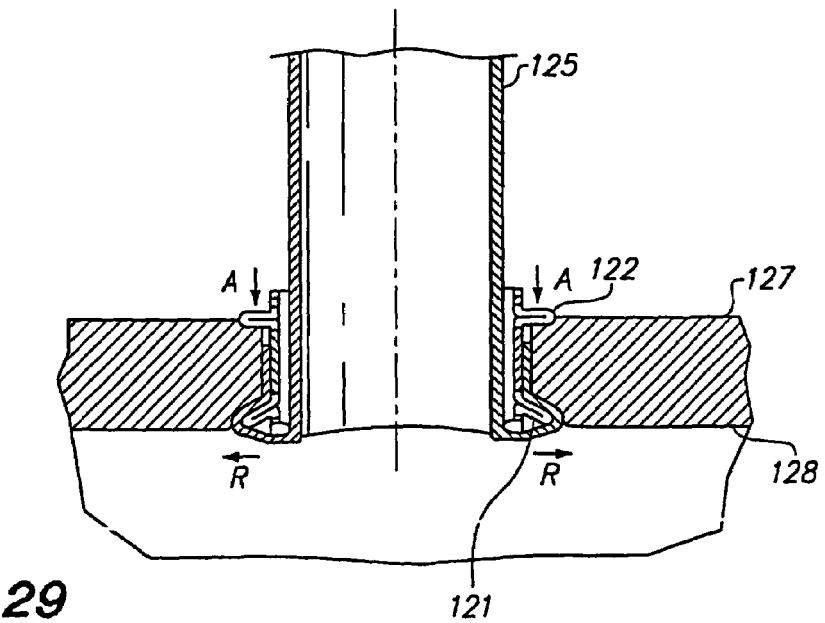
FIG. 29 is an transverse cross sectional view of an alternative embodiment of the large vessel stent having a distal flange angled toward the distal end of the stent.

In the embodiment illustrated in FIG. 14, the helical members have deflecting sections 153 on the proximal and distal ends, and an intermediate deflecting section located substantially centrally along the length of the helical member between the proximal and distal ends of the helical member. In the deployed flange, the intermediate deflecting section is thus located on a peripheral extremity of the deployed flange and the flange is substantially perpendicular to the stent longitudinal axis. Alternatively, the intermediate deflecting section may be located distally or proximally along the length of the helical member, so that the flange is angled relative to the longitudinal axis of the stent. For example, where the intermediate deflecting section is located between the center point and the distal end of the helical member, the flange is angled toward the distal end of the large vessel stent 110, as illustrated in FIG. 29.

In the embodiment of the large vessel stent illustrated in FIGS. 18–20, the length of the large vessel stent before deployment of the flanges is greater than the width of the target vessel wall, so that the deformable sections are on either side of the target vessel, at least in part outside of the incision in the target vessel wall. The length of the stent after the flanges are deployed, as illustrated in FIG. 20, is substantially equal to the width of the target vessel wall. The length of the stent 110 is about 0.5 mm to about 5 mm, and the diameter is about 4 mm to about 10 mm. The large vessel stent is preferably formed from stainless steel. However, other suitable materials may be used, including tantalum, titanium, and alloys thereof. The large vessel stent wall thickness is about 0.10 mm to about 0.20 mm.

Figure 30:
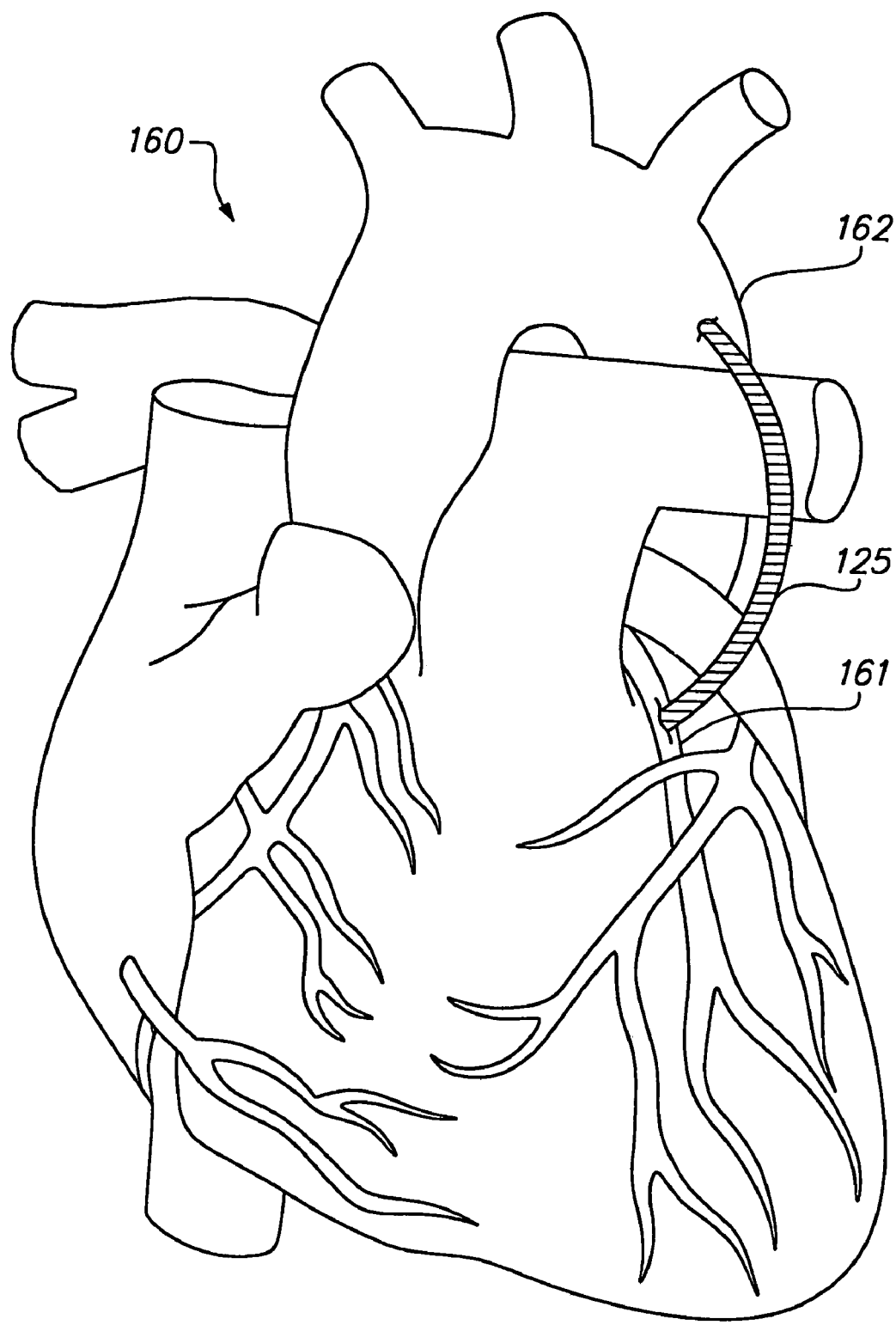
FIG. 30 is an elevational view of a human heart having a graft vessel attached thereto.

The anastomotic stents of the invention may be used for a variety of anastomosis procedures, including coronary bypass surgery. For example, the distal end of a dissected mammary artery can be connected to a coronary artery, using a small vessel stent of the invention. Typically, one or more slices are made in the end of the mammary artery in order to increase to diameter of the mammary artery to facilitate its connection to the outer flange of the small vessel stent. FIG. 30 illustrates a heart 160 on which a coronary bypass has been performed using the anastomotic stents of the invention. The distal end of a harvested vein graft 125 is connected to the coronary artery 161 using a small vessel stent of the invention, and the proximal end of the graft vessel is connected to the descending aorta 162 using a large vessel stent of the invention.

In an anastomotic system using the large vessel stent in combination with the small vessel stent, the large vessel stent would preferably be connected to the target vessel first, so that the lumen of the graft vessel would be accessible through the other end of the graft vessel, to thereby provide access for a catheter which incises and expands the aortal wall. The small vessel stent would be connected next, because it requires no access through the lumen of the graft vessel.

Although principally discussed with respect to coronary bypass surgery, the anastomotic stents of the invention may be used in a number of anastomosis procedures. For example, the other types of anastomosis procedures include, femoral-femoral bypass, vascular shunts, subclavian-carotid bypass, organ transplants, and the like.

It will be apparent from the foregoing that, while particular forms of the invention have been illustrated and described, various modifications can be made without departing from the spirit and scope of the invention. For example, those skilled in the art will recognize that the large and small vessel stents of the invention may be formed of wound or bended wire, filaments and the like. Other modifications may be made without departing from the scope of the invention.

What is claimed is:

1. An anastomosis tool for connecting a graft vessel to a target vessel, comprising:
   a one-piece anastomosis device having a diameter;
   a first tube configured to receive said anastomosis device;
   a second tube, said first and second tubes movable with respect to one another to deploy said anastomosis device, wherein the diameter of said anastomosis device increases upon deployment; and
   a side hole in at least one of said first and second tubes configured to allow the graft vessel to pass out of the side of said tube.

2. The anastomosis tool of claim 1, wherein said second tube is rotatable with respect to said first tube.

3. The anastomosis tool of claim 1, wherein said second tube is movable with respect to said first tube to apply torque to said anastomosis device.

4. The anastomosis tool of claim 1, wherein said second tube is movable with respect to said first tube to apply an axial compressive force to said anastomosis device.

5. The anastomosis tool of claim 1, wherein said first tube is removably connectable to said anastomosis device.

6. The anastomosis tool of claim 1, further comprising a handle connected to said first and second tubes with a mechanism for deploying said anastomosis device.

7. The anastomosis tool of claim 1, wherein said first tube includes a plurality of connecting members at a distal end thereof and said anastomosis device includes a plurality of features arranged to removably connect to said plurality of connecting members.

8. The anastomosis tool of claim 1, wherein said first tube and said second tube are substantially concentric.

9. A method of performing anastomosis between a graft vessel and a target vessel, the method comprising:
 receiving an anastomosis device on an anastomosis device applicator having a substantially rigid vessel penetrating member;
 connecting a graft vessel to the anastomosis device on the anastomosis device applicator;
 penetrating a target vessel with the vessel penetrating member of the anastomosis device applicator;
 advancing the anastomosis device into the penetration in the target vessel;
 deploying the anastomosis device with the anastomosis device applicator to connect the graft vessel to the target vessel; and
 maintaining the anastomosis device applicator and vessel penetrating member outside of the lumen of the graft vessel during the receiving, connecting, penetrating, advancing and deploying.

10. The method of claim 9, wherein the step of deploying the anastomosis device is performed by moving two tubes of the anastomosis device applicator with respect to one another to deploy the anastomosis device.

11. The method of claim 9, wherein the anastomosis device is a one-piece anastomosis device.

12. The method of claim 9, wherein during the penetrating step the vessel penetrating member is positioned inside the anastomosis device applicator.

13. The method of claim 9, wherein the step of deploying connects an end of the graft vessel to a side of the target vessel.

14. A method of performing anastomosis between a graft vessel and a target vessel, the method comprising:
 providing a one-piece anastomosis device;
 receiving said anastomosis device on an anastomosis device applicator including a first tube and a second tube;
 connecting a graft vessel to said anastomosis device on the anastomosis device applicator with an end of the graft vessel passing out a side hole of at least one of the first and second tubes; and
 deploying said anastomosis device with the anastomosis device applicator to connect the graft vessel to the target vessel, wherein said deploying increases the diameter of said anastomosis device.

15. The method of claim 14, wherein said deploying said anastomosis device is performed by moving the first and second tubes with respect to one another.

16. The method of claim 14, wherein said receiving said anastomosis device on the anastomosis device applicator is performed by removably connecting a plurality of features of said anastomosis device to a plurality of connecting members at a distal end of the first tube.

* * * * *